US009365525B2

(12) United States Patent
Manesh et al.

(10) Patent No.: US 9,365,525 B2
(45) Date of Patent: Jun. 14, 2016

(54) SYSTEM AND METHOD FOR EXTRACTION OF CHEMICALS FROM LIGNOCELLULOSIC MATERIALS

(71) Applicant: American Science and Technology Corporation, Chicago, IL (US)

(72) Inventors: Ali Manesh, Chicago, IL (US); Reza Hemyeri, Thousand Oaks, CA (US); Susanta Mohapatra, Wausau, WI (US); John Guenther, Merrill, WI (US); Edwin Zoborowski, Wausau, WI (US); Mohammad Ali Manesh, Chicago, IL (US)

(73) Assignee: American Science and Technology Corporation, Chicago, IL (US)

( * ) Notice: Subject to any disclaimer, the term of this patent is extended or adjusted under 35 U.S.C. 154(b) by 684 days.

(21) Appl. No.: 13/764,181

(22) Filed: Feb. 11, 2013

(65) Prior Publication Data
US 2014/0227161 A1 Aug. 14, 2014

(51) Int. Cl.
*B01D 11/04* (2006.01)
*C08B 30/04* (2006.01)
(Continued)

(52) U.S. Cl.
CPC .......... *C07D 265/30* (2013.01); *B01D 11/0488* (2013.01); *B01D 11/0492* (2013.01);
(Continued)

(58) Field of Classification Search
CPC .. B01B 11/02; B01B 11/028; B01B 11/0284; B01B 11/0288; B01B 11/04; B01B 11/0488; B01B 11/0492; C08B 1/00; C08B 30/04; C08B 30/042; C08B 37/00; C08B 37/0003; C10L 1/1802; C10L 1/182; C10L 1/184;
C10L 2200/046; C10L 2200/0476; C10L 2200/0484; C10L 211/13; C08L 97/00; C08L 97/005; C08L 97/02; C08H 8/00; C07G 1/00; C07C 27/00; C07C 27/34; C07C 41/01; C07C 41/50; C07C 45/00; C07C 51/00; C07C 67/00; C07C 67/08; C07C 69/14; C07C 69/716; C07C 43/303; C07C 43/04; C07D 65/30
USPC .......... 44/305, 307, 313, 605; 127/36, 42, 43, 127/46.1; 162/14; 210/634, 639, 774, 805; 435/161, 163–165; 530/500, 507; 560/179, 265, 607; 585/240, 242; 544/106

See application file for complete search history.

(56) References Cited

U.S. PATENT DOCUMENTS 3,776,897 A 12/1973 Ikari et al.
4,397,712 A 8/1983 Gordy
(Continued)

OTHER PUBLICATIONS

Zhao, Cheng and Liu, Organosolv Pretreatment of Lignocellulosic Biomass for Enzymatic Hydrolysis, Applied Microbiology and Biotechnology, 82:815-827, Springer-Verlag (2009).
(Continued)

*Primary Examiner* — Joseph Drodge
(74) *Attorney, Agent, or Firm* — Beem Patent Law Firm

(57) ABSTRACT

An organosolv process for producing bio-products by decomposing lignocellulosic materials comprises providing an initial lignin solvent with water, an acid, and a lignin dissolving chemical comprising at least one of an organic ester, butyl acetate, an organic furan, and furfural. The process also includes placing the lignin solvent in contact with a biomass to form a circulation solvent, and recycling at least a portion of the circulation solvent by circulating the circulation solvent back into contact with the biomass. The circulating of the circulation solvent occurs for a period of time, after which, the process then includes separating material such as chemicals and lignin from the circulation solvent. The chemicals can be recycled as new solvent or sold while lignin can be used as natural and renewable colorant for polymers such as poly lactic acid.

37 Claims, 10 Drawing Sheets

Process Flow Diagram, Organosolv Based Cellulosic Bio-Fuel

(51) Int. Cl.
| | |
|---|---|
| *C08B 37/00* | (2006.01) |
| *C07D 265/30* | (2006.01) |
| *C07C 45/00* | (2006.01) |
| *C07C 51/00* | (2006.01) |
| *C07C 67/00* | (2006.01) |
| *C08H 8/00* | (2010.01) |
| *C08H 7/00* | (2011.01) |
| *C07C 67/08* | (2006.01) |
| *C07C 41/01* | (2006.01) |
| *C07C 41/50* | (2006.01) |
| *C07C 27/00* | (2006.01) |

(52) U.S. Cl.
CPC ............. *C07C27/00* (2013.01); *C07C 41/01* (2013.01); *C07C 41/50* (2013.01); *C07C 45/00* (2013.01); *C07C 51/00* (2013.01); *C07C 67/00* (2013.01); *C07C 67/08* (2013.01); *C08B 30/04* (2013.01); *C08B 37/0003* (2013.01); *C08H 6/00* (2013.01); *C08H 8/00* (2013.01)

(56) References Cited

U.S. PATENT DOCUMENTS

| | | | |
|---|---|---|---|
| 4,470,851 | A | 9/1984 | Paszner et al. |
| 4,511,433 | A | 4/1985 | Tournier et al. |
| 4,536,584 | A | 8/1985 | Eskamani et al. |
| 4,746,401 | A | 5/1988 | Roberts et al. |
| 4,764,627 | A | 8/1988 | Diebold et al. |
| 4,793,898 | A | 12/1988 | Laamanen et al. |
| 5,026,808 | A * | 6/1991 | Schroeder ............... 527/400 |
| 5,049,236 | A | 9/1991 | Dimmel et al. |
| 5,091,054 | A | 2/1992 | Meier et al. |
| 5,246,543 | A | 9/1993 | Meier et al. |
| 5,424,417 | A | 6/1995 | Torget et al. |
| 5,503,996 | A | 4/1996 | Torget et al. |
| 5,705,369 | A | 1/1998 | Torget et al. |
| 5,788,812 | A | 8/1998 | Agar et al. |
| 6,007,678 | A | 12/1999 | Linsten et al. |
| 6,019,870 | A | 2/2000 | Devic et al. |
| 6,022,419 | A | 2/2000 | Torget et al. |
| 6,165,308 | A | 12/2000 | Chen et al. |
| 6,214,164 | B1 | 4/2001 | Rantala |
| 6,398,908 | B1 | 6/2002 | Hermansson et al. |
| 6,503,369 | B2 | 1/2003 | Rousu et al. |
| 6,692,578 | B2 | 2/2004 | Schmidt et al. |
| 6,824,645 | B2 | 11/2004 | Jaschinski et al. |
| 6,923,887 | B2 | 8/2005 | Pan |
| 7,465,791 | B1 | 12/2008 | Hallberg et al. |
| 7,931,784 | B2 | 4/2011 | Medoff |
| 7,932,065 | B2 | 4/2011 | Medoff |
| 8,017,818 | B2 | 9/2011 | Cortright et al. |
| 8,053,566 | B2 | 11/2011 | Belanger et al. |
| 8,053,615 | B2 | 11/2011 | Cortright et al. |
| 8,083,906 | B2 | 12/2011 | Medoff |
| 8,137,628 | B2 | 3/2012 | Cheiky et al. |
| 8,142,620 | B2 | 3/2012 | Medoff |
| 8,143,464 | B2 | 3/2012 | Cheiky et al. |
| 8,168,038 | B2 | 5/2012 | Medoff |
| 8,168,840 | B2 | 5/2012 | Brady et al. |
| 8,173,406 | B1 | 5/2012 | Wang et al. |
| 8,193,324 | B2 | 6/2012 | Hallberg et al. |
| 2004/0231060 | A1 | 11/2004 | Burdette et al. |
| 2008/0196847 | A1 | 8/2008 | Pieter van Heiningen et al. |
| 2009/0090478 | A1 | 4/2009 | Hollomon et al. |
| 2009/0118477 | A1 | 5/2009 | Hallberg et al. |
| 2009/0145021 | A1 | 6/2009 | Guay et al. |
| 2010/0043782 | A1 * | 2/2010 | Kilambi et al. ............ 127/1 |
| 2010/0249390 | A1 | 9/2010 | Azuma et al. |
| 2010/0279361 | A1 | 11/2010 | South et al. |
| 2011/0192072 | A1 * | 8/2011 | Steele et al. ............ 44/307 |
| 2012/0116063 | A1 * | 5/2012 | Jansen et al. ............ 530/507 |
| 2013/0023702 | A1 * | 1/2013 | Qiao et al. ............ 568/959 |
| 2013/0118059 | A1 * | 5/2013 | Lange et al. ............ 44/307 |
| 2014/0242867 | A1 * | 8/2014 | Jansen et al. ............ 442/181 |
| 2014/0275501 | A1 * | 9/2014 | Capanema et al. ........... 530/500 |
| 2014/0326422 | A1 | 11/2014 | Fallon et al. |
| 2015/0107790 | A1 | 4/2015 | Sixta et al. |
| 2015/0176031 | A1 * | 6/2015 | Streffer |

OTHER PUBLICATIONS

Drljo, Weinwurm and Friedl, Evaluation and Optimization of Organosolv Process, Thermal Process Engineering, Vienna Institute of Technology, Institute of Chemical Engineering (2012).

Cybulska, Lei, Julson and Brudecki, Optimization of Modified Clean Fractionation of Prairie Cordgrass, Int'l J. of Agric. and Biol. Eng.5. 2, 1-10 (Jun. 2012).

Hergert and Pye, Recent history of organosolv pulping, Solvent Pulping Symposium, 9-26 (1992).

Vallejos, Felissia, Curvelo, Zambon, Ramos and Area, Chemical and Physico-Chemical Characterizations of Lignins obtained from ethanol-water fractionation of bagasse, Bio Resources 6(2), 1158-1171 (2011).

Huijgen, De Wild and Reith, Lignin Production by Organosolv fractionation of lignocellulosic biomass, Energy Research Center of the Netherlands, International Biomass Valorization Congress, Sep. 13-15, 2010.

Huijgen, Laan and Reith, Modified organosolv as a fractionation process of lignocellulosic biomass for co-production of fuels and chemicals, 16th European Biomass Conference and Exhibition, 2-6, Valencia Spain (Jun. 2008).

* cited by examiner

Process Flow Diagram, Organosolv Based Cellulosic Bio-Fuel

SYSTEM AND METHOD FOR EXTRACTION OF CHEMICALS FROM LIGNOCELLULOSIC MATERIALS

BACKGROUND OF THE INVENTION

1. Field of the Invention

The subject matter herein is generally directed to delignification and fractionation of a biomass using organosolv processes, and particularly to such organosolv processes that include recycling of organic products from the fractionation process and for use in a solvent placed in contact with a biomass.

2. Description of the Related Art

Several attempts have been made to apply an organosolv fractionation process that recycles certain chemicals from lignin solvent used to delignify lignocellulosic materials and produce cellulose or fiber for C6 sugar that can be converted to renewable chemicals, biofuels and other sugar based products. One of the major drawbacks for this type of fractionation process is that solvent recovery may be limited, which directly affects the economic feasibility of the process. Therefore, there exists a need for a system that can maintain or regenerate solvent during a delignification process to increase economic viability.

Another economic drawback is that the cost of the fractionation of biomass typically is higher than the financial benefits realized from producing cellulose fiber alone. In other words, to have a profitable process, nearly all of the biomass should be used up, ideally with near zero waste, to produce more amounts of organic products in addition to the fibers. Thus, a desire exists to provide an organosolv process that can readily produce different and more classes of biochemicals during a fractionation process.

SUMMARY OF THE INVENTION

The deficiencies mentioned above are resolved by the organosolv fractionation process disclosed herein. Generally, the process is directed to the use of biomass materials in a reactor with an initial lignin solvent that has two partially miscible acidic liquids one being a lignin dissolving compound (herein referred to as the lignin dissolving chemical even though it may include or be formed from multiple chemicals), the other being water or recycled water, and cooking them under autoclave conditions for a certain period of time. After the initial solvent is placed in contact with the biomass by running the initial lignin solvent on, over, or through the biomass, the reaction with the biomass results in a circulation solvent that includes organic material, lignin, and other chemicals that can then be re-circulated back into contact with more biomass or biomass still remaining in the reactor and for further transformation of the solvent into usable compounds and chemicals that can be used to produce final products such as renewable chemicals, pure lignin, and cellulose. After a period of time, part or all of the resulting solvent is removed and settled or separated into further organic material and aqueous parts that can be recycled or reused in the next initial lignin solvent for a new biomass. With the use of self-sustaining chemicals such as butyl acetate and/or furfural forming at least a portion of the initial lignin dissolving chemical or the separated organic material part reused for a new biomass, the fractionation process becomes very efficient.

Specifically, by one approach, an organosolv process for producing bio-products by decomposing lignocellulosic materials comprises providing an initial lignin solvent comprising water, an acid, and a lignin dissolving chemical comprising at least one of an organic ester, butyl acetate, an organic furan, and furfural. In this process, the lignin solvent is then placed in contact with a biomass to form a circulation solvent. The process then involves recycling at least a portion of the circulation solvent by circulating the circulation solvent back into contact with the biomass, and circulating the circulation solvent for a period of time. After the period of time, the process includes separating material from the circulation solvent. The lignin dissolving chemical for the initial lignin solvent may include butanol combined with a butyl ester, an organic furan, or both.

By another approach, an organosolv process for producing bio-products by decomposing lignocellulosic materials comprises providing a first initial lignin solvent comprising water, an acid comprising acetic acid, sulfuric acid, or both, and a lignin dissolving chemical. Next, the process includes placing the first initial lignin solvent in contact with a first biomass to form a circulation solvent, and then recycling at least a portion of the circulation solvent by circulating the circulation solvent back into contact with the biomass, and circulating the circulation solvent for a period of time. After the period of time, the circulation solvent is divided into an aqueous portion, an organic material portion, and lignin. At least a portion of the aqueous portion, the organic material portion, or both are reused in an initial lignin solvent to be placed in contact with a new biomass. In one form, the lignin dissolving chemical of the first initial lignin solvent is butanol. By another form, the reused organic material portion for use with a new biomass includes a butyl ester, organic furfural, or both.

DETAILED DESCRIPTION OF THE PREFERRED EMBODIMENTS

Figure 1:
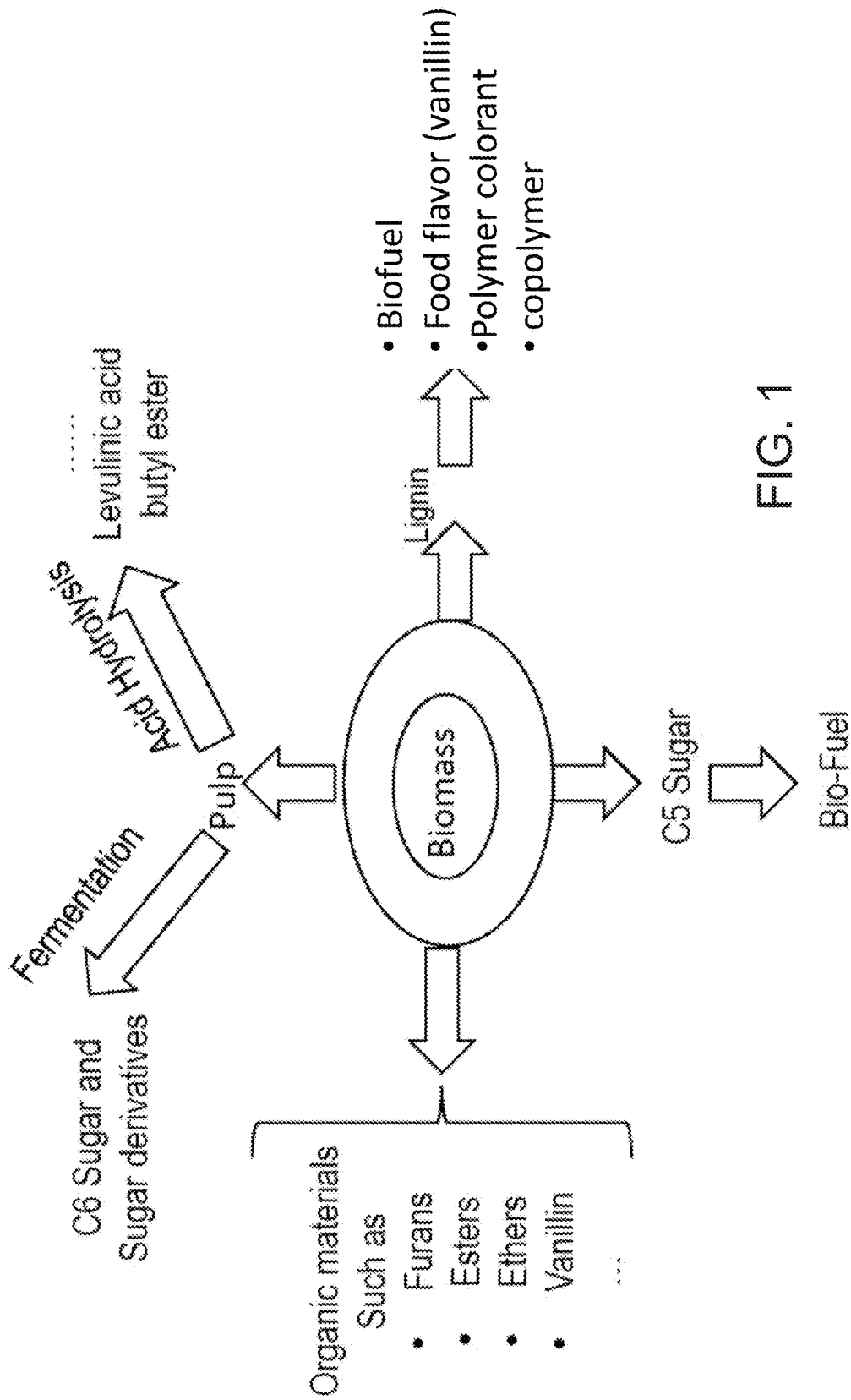
FIG. 1 is a diagram of a biomass fractionation process and some of the products produced therefrom.

Disclosed herein is a temperature, pressure, and time controlled, organosolv fractionation process that uses a solvent to interact an acid and a lignin dissolving chemical with a biomass material to separate the lignin from cellulose and hemicellulose in the biomass material, resulting in a number of different chemicals, organic materials, and/or products. To increase the efficiency of the process, certain materials within the solvent are consumed as much as possible by placing an initial lignin solvent on the biomass and then recycling the resulting solvent (referred to herein as the circulation solvent) back onto the biomass as described herein. This recycling may be performed with very little, if any, processing of the circulation solvent. Thus, the resulting liquor and lignin forming the circulation solvent may be recycled back onto the biomass without any distillation of its chemicals.

It was also discovered that the use of certain lignin dissolving chemicals will increase the efficiency of the process. Such lignin dissolving chemicals includes a butyl ester such as butyl acetate and an organic furan such as furfural, for example. Both of these chemicals may be more efficient than pure butanol because, for example, they produce more 2-furancarboxaldehyde, 5-(hydroxymethyl) than butanol, and which is used to make biofuel. Butyl acetate in the initial lignin solvent also produces more furfural than that produced by butanol, and furfural used as the initial lignin solvent extracts more lignin than pure butanol. See Example 5 below. Thus, butyl ester or organic furan alone, or the two chemicals combined may be used as the lignin dissolving chemical for an initial lignin solvent used on a new biomass to increase efficiency over the use of pure butanol. However, using one or both of these chemicals alone or combined as the lignin dissolving chemical in the initial lignin is not as cost efficient as using these chemicals mixed or combined with butanol.

Specifically, it has been found that the process can be even more efficient and cost effective by combining the butyl ester, organic furan, or both with butanol in the initial lignin solvent because butyl acetate and furfural have self-sustaining properties. Thus, for example, and based on the experimentation performed, the combination of butanol, process heat, pressure, and time break down the available hemicellulose into furfural and acetic acid. Butanol combined with acetic acid forms a butyl ester such as butyl acetate. Since both furfural and butyl acetate are lignin dissolving chemicals, their production by the use of butanol adds to the amount of organic solvent (or lignin dissolving chemicals) in the process, and particularly in a recycled or circulating solvent. The process may take advantage of this by immediately recycling the chemicals back over the biomass.

Moreover, the process can become much more efficient by also using the produced lignin dissolving chemicals obtained from the resulting circulation solvent for use in an initial lignin solvent in the next new biomass placed in a reactor. For instance, once the circulation is complete for a biomass currently in the reactor, the circulation solvent may be separated into parts including an aqueous solution portion, an organic material portion, and lignin. The organic material portion and aqueous solution portion may then be reused for the initial lignin solvent to be circulated over the next new biomass (or batch if a batch process is used). The organic material portion and aqueous solution portion may be placed in the new initial lignin solvent without further separating or processing. Alternatively, for example, the organic material portion may be further distilled as explained below to obtain certain chemicals such as the produced butyl ester or organic furan or both. Then, when desired, just these certain chemicals may be used as the lignin dissolving chemicals in a new initial lignin solvent for the next new biomass. The reused chemicals may form the entire next initial lignin solvent or may reduce the amount of fresh solvent chemicals such as butanol necessary for continuing the process over multiple or many subsequent new biomasses.

In more detail, one mole of acetic acid (about 60 g) obtained from the biomass feedstock plus one mole of butanol (about 74 g) produces one mole of butyl ester (116 g). Since butyl ester is a lignin dissolving chemical, adding about 116 g butyl ester instead of about 74 g of butanol back into the next initial lignin solvent to fractionate a new biomass will effectively increase the solvent by about 42 g (about 56.75% gain or about 60% gain). Stated another way, the increase in solvent by using a butyl ester such as butyl acetate instead of butanol, increases solvent by about 40-44 g (or by about 57%, or generally about 60%, or about 54% to about 60%). In a similar parallel reaction, 1 kg of biomass feedstock produces about 0.25 kg of furfural (or about 0.2-0.3 kg of furfural). The process of generating additional furfural and/or butyl ester assists to produce more solvent as the process progresses, and at the end of the process, some of the extra solvents can be extracted for sale or other uses if not to be reused in the next or subsequent initial solvent to fractionate a new biomass. This may cover the cost of fresh butanol when the butanol and butyl acetate are generally the same price.

By this approach, in one form, butanol may be used as the lignin dissolving chemical in a first initial lignin solvent for a first biomass. This may occur when a factory first opens or a production line has its very first run, or after restarting the production line after a complete shut down and cleaning of the production line, for example. Thereafter, however, the initial lignin solvent composition for each new biomass (or new batch in a batch process) may be a mixture of butanol with butyl ester (butyl acetate for example) and/or organic furan (furfural for example) and/or any other lignin solvent produced and obtained from the circulation solvent produced during fractionation of the previous biomass. In one form, the lignin dissolving chemical in each initial lignin solvent includes about ⅓ butanol, ⅓ butyl ester, and ⅓ furfural, by weight, and fresh butanol is added as needed to generally or substantially maintain these proportions. Of course, fresh or reused butyl ester and/or organic furan may be added or removed as needed to maintain the ⅓ parts as desired as well.

Other alternatives are contemplated depending on the results desired such that the proportions may be different than the ⅓ parts. For example, when more solvent production is desired, a higher proportion of butanol may be used in the lignin dissolving chemical for the initial lignin solvent. Otherwise, a larger proportion of the other chemicals, such as butyl ester and furfural, may be used in the lignin dissolving chemical instead of butanol when it is desirable to produce more derivative products, such as 2-furancarboxaldehyde, 5-(hydroxymethyl), for example, from the chemical reactions using butyl ester and furfural, and that can be removed out of the system and sold. This process may or may not include providing the first initial lignin solvent with lignin dissolving chemicals of any of the mixtures mentioned herein rather than only butanol. Thus, it will be understood that while the lignin dissolving chemicals in the initial lignin solvent may be butanol, butyl acetate, or furfural alone, it may alternatively be any mixture of these including butanol and butyl acetate, butanol and furfural, butyl acetate and furfural, or the mixture of all three chemicals mentioned above, or the mixture of all three chemicals mentioned above and other organic chemicals produced as a result of the reactions as presented in FIGS. 7, 9 and 10 (such as formic acid, butyl ester; n-butyl ether; 2-furancarboxaldehyde, 5-(hydroxymethyl); butyl ester; butane, 1,1-dibutoxy; pentanoic acid, 4-oxo-butyl ester (levulinic acid, butyl ester); vanillin; and pheno, 2-methoxy-4-propyl (homovanillyl alcohol) to name a few examples).

The acetic acid remaining in an aqueous part of the circulation solvent also may be reused for the next initial lignin solvent. Thus, the acid selected for the initial solvent can also improve the process. In one form, using acetic acid instead, or in addition to, sulfuric acid in the initial lignin solvent will produce more butyl acetate although less furfural.

By also varying the conditions or parameters of the process, the process may become more efficient. For example, the process increases production of butyl ester when the process uses temperatures approximately at or higher than 178° C. As the operating temperature increases, the process increases production of resulting chemicals such as formic acid, n-butyl ether, butyl ester, pentanoic acid, vanillin, and other organic chemicals. At such a relatively higher temperature, more lignin is extracted from the raw biomass materials, and in turn, more dissociated cellulose fibers exist on the biomass, for example, and therefore, the remaining pulp better facilitates sugar production.

Raising the temperature even higher, and more specifically, at approximately 225° C., according to another aspect, provides for simultaneous fractionation of lignocellulosic materials and hydrolysis of cellulose. By raising the process temperature to this level, lignin degrades and forms other chemicals like vanillin, while most of the resulting pulp from the biomass is further fractionated to other chemicals such as levulinic acid, butyl ester, or other organic chemicals, such as char. The use of these very high temperatures also tend to result in condensation of two butanol molecules to produce n-dibutyl ether, and converts more sugar into other organic chemicals so that less sugar remains in the aqueous layer or resulting liquor of the process.

In another form, the process uses an increased reaction time interval where the mixture of ingredients are held in a reactor described below, such as approximately at least 30 minutes for one example, or approximately 30 minutes in another example, and where the increased time period may increase the production of butyl acetate and remove more lignin from the biomass. In other forms, adequate time periods may be 25-35 min or 30-40 minutes for example. As the operation time increases, more acetic acid, by one example, converts to chemicals such as butyl ester, vanillin, furfural, or other organic materials.

According to another aspect, the process increases the production of vanillin by performing the fractionation in an atmosphere of higher pressure such as at least approximately 80 to 120 PSI, alternatively 90 to 110 PSI, and preferably 100 PSI (all of the PSI measurements herein are gauge measurements unless otherwise noted). As the operating pressure and time increase, more acetic acid, for example, is converted to organic materials and, as a result, this increases the production of the resulting chemicals such as formic acid, n-butyl ether, 2-furancarboxaldehyde, pentanoic acid, vanillin, and so forth.

In a further form, the process uses about five to fifteen grams of solvent per every one gram of lignocellulosic material. In another form, the process uses a ratio of about five to one grams solvent to biomass.

Biomass Fractionation Process

Now in more detail, cellulosic feedstock that form the biomass used by the process may include a wide variety of material such as agricultural wastes, forestry products, forestry wastes, cellulosic rich municipal wastes, or other cellulose rich industrial wastes, and more specifically, materials ranging from wood, wood chips, bagasse, grass, corn stover, corn stalks, bark, straw, specialty biofuel crops, and pulp mill sludge as good sources of sugars to convert into bio-based products such as ethanol, butanol, isoprene, or lactic acid to name a few examples. The main problem with cellulose as a feedstock is releasing the cellulose itself. In a plant, cellulose is encased in the lignin, analogous to the way that a steel reinforcing rod is encased in concrete. The lignin is the substance that gives wood its strength. To release the cellulose from the lignin, by one approach, the lignin may be dissolved in some kind of organic solvent.

In one form, the organosolv based fractionation process used to dissolve the lignin here includes mixing biomass and solvent in a pressurized reactor at a certain temperature for a certain time and under a certain atmosphere. This results in production of organic materials, lignin, fiber, and some sugar.

Referring to FIG. 1, one advantage of this organosolv process is that all the fractions may be collected separately and utilized separately to make this process more selective and profitable. In other words, when organic lignin solvent is being used with water and acid as the solvent, the fractionation process for a biomass ultimately produces solid fibers and a resulting solvent mixture, which in one form, may be mainly a liquid. In a settling or separating tank, the solvent separates into two layers including an upper organic layer (the liquor) and a lower aqueous layer. The organic layer substantially includes all organic materials left over from the original or initial input solvent plus all the organic materials made during the process as well as lignin that is dissolved in all of these organics materials. The aqueous layer includes some sugar, acetic acid, and some traces of organic materials based on their solubility in water. Thus, the process is adaptable because the materials produced from the fractionation can be separated and removed easily to produce a desired resulting chemical or product.

Also, the fractionation process here can be controlled to produce combinations of products. For example, the biomass, acid, and lignin dissolving chemical in the solvent, when mixed and heated under pressure, may separate lignin from lignocellulosic materials and dissolve it within the circulating solvent. When the lignin is separated from the solvent, the lignin can be used in a small quantity like 5% as colorant for polymers such as poly lactic acid, or in a larger quantities mixed with other polymers as copolymer to produce polymeric parts, or for production of vanillin, bio-fuels, and other products, or as a natural polymer to be used in plastic industries. C5 sugar dissolved in the aqueous layer may also be obtained for use in manufacturing biofuels. The resulting pulp may be fermented into C6 sugars and sugar derivatives, or submitted to acid hydrolysis to form Levulinic acid, Levulinic ester, butyl ester, for example. Other organic materials that may be produced from the separated organic material or layer include Furans, Esters, Ethers, and Vanillin, which may be used as a solvent (the lignin dissolving chemical) to continue the fractionation process, or separated and sold as organic chemicals.

Figure 2:
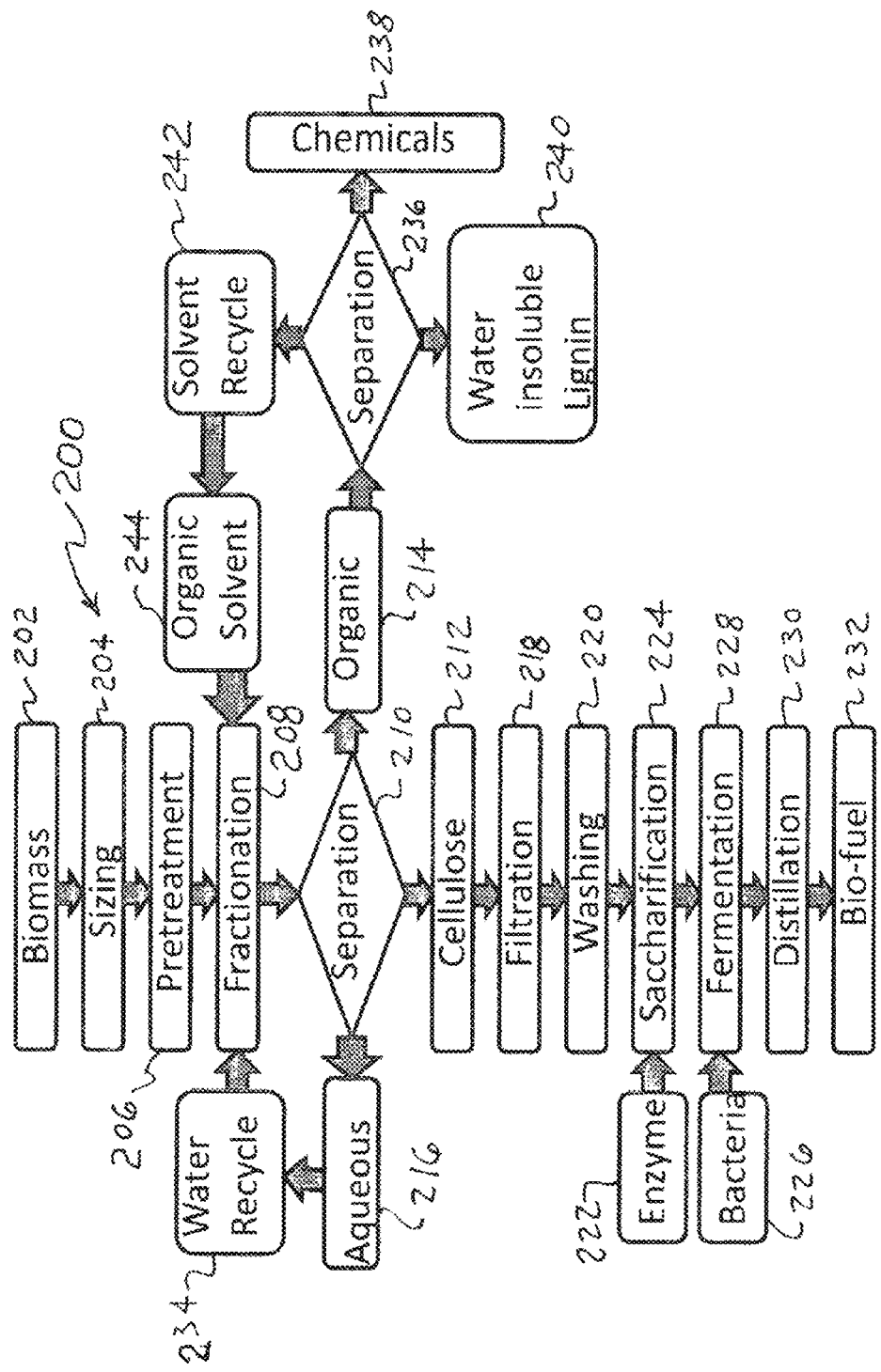
FIG. 2 is a process flow diagram of an organosolv-based, cellulosic, bio-fuel process.

Referring to FIG. 2, an organosolv process 200 includes obtaining 202 the biomass, and sizing 204 the biomass by chopping, cutting, and so forth, and using screens or sieves until, by one example, biomass pieces of approximately 0.5 inch by 0.25 inch by 1.0 inch are obtained. Other alternatives include about 0.4-0.6 inches by about 0.2-0.3 inches by about 0.9-1.1 inches. Next, the pieces may be pre-treated 206 by soaking them for a few hours or overnight in water to obtain uniform moisture content by one approach. Thereafter, the biomass pieces are placed in the reactor 1.

Figure 3:
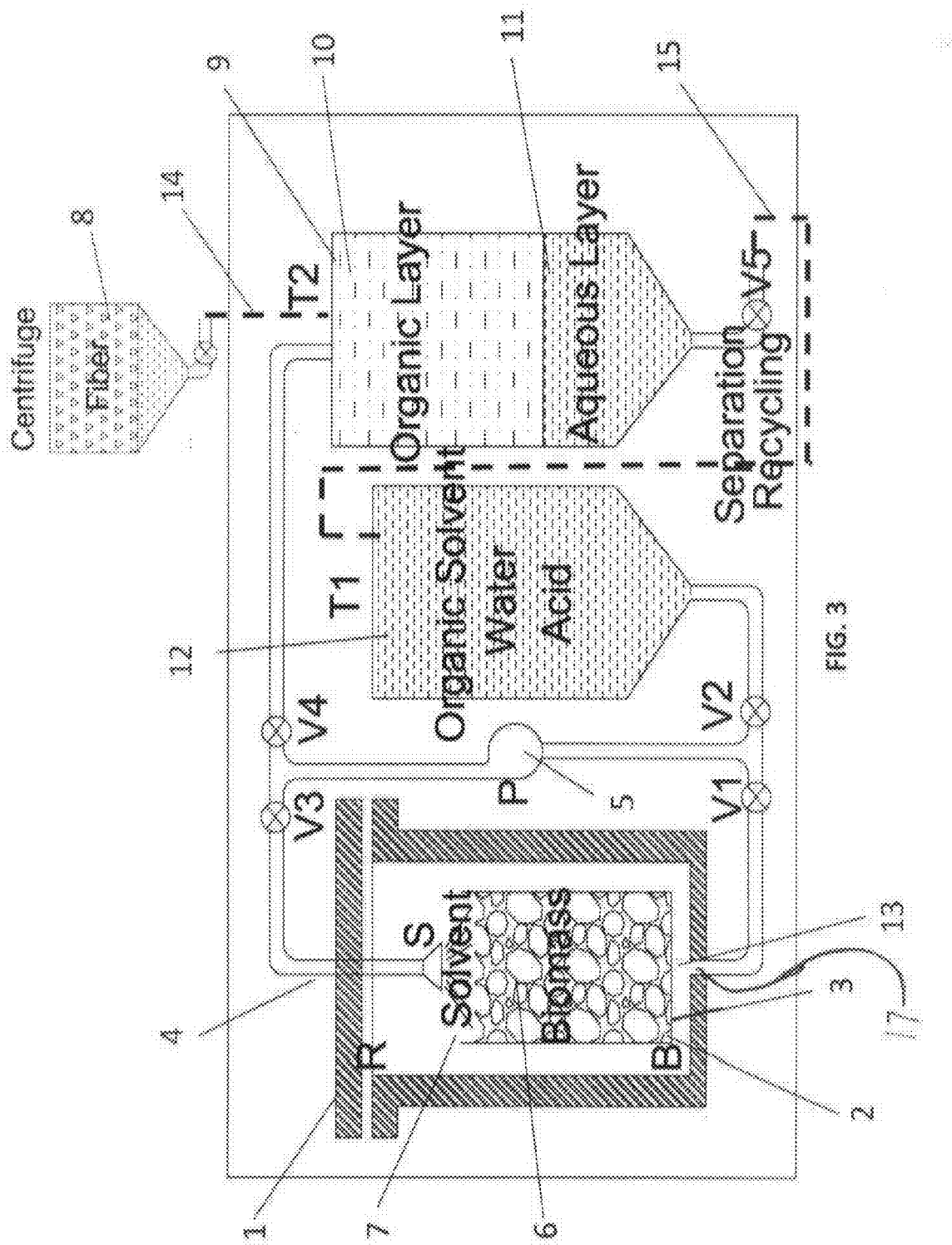
FIG. 3 is a diagram of a bio-refinery fractionation reactor system using the process of FIG. 2.

Referring to FIGS. 2-3, the organosolv processes herein may use continuous or batch processes in an autoclave-type fraction environment. An example of a batch reactor is the reactor 1 that is fluidly connected by valves V1 to V4 to a separation or settling tank 9 (T2) and an initial solvent tank 12 (T1). Specifically, for the start of each new batch, biomass pieces are placed in the reactor 1. Then, initial lignin solvent is provided from the solvent tank 12 via pump 5, and by opening valves V2 and V3 and closing valves V1 and V4. This delivers the initial solvent to an inlet, or in this case to the top, of the reactor 1. The initial solvent then is placed in contact with the biomass in the reactor and flows on or over the biomass until it reaches an outlet of the reactor. Valve V1 opens and valve V2 closes to allow circulation solvent to flow from the outlet or bottom of reactor 1 back to the inlet or the top of reactor 1 as described below. At the end of the process, valve V3 closes and valve V4 opens (and valve V1 is already opened) to transfer the final or resulting circulation solvent 13 to the separation tank 9. A valve V5 may be provided as an outlet to collect material from the separation tank 9 which may then be poured into the initial solvent tank 12 (T1) for reuse in the initial lignin solvent for a new batch of biomass in the reactor 1. Otherwise, the collected material from the separation tank 9 (T2) may be taken away for further processing toward an end product. Alternatively, valve V5 may control an outlet to the exterior of the system and/or a flow path 15 (or pipe or tubing shown in dashed line for example) back to the initial solvent tank 12 (T1) for reuse of the separated material when no further processing is necessary. In one form, however, the organic material, or the liquor, may be distilled to remove butyl esters and organic furan, for example, so that just the lignin dissolving chemicals, or specified amounts of the lignin dissolving chemicals, are reused and placed into the initial solvent tank 12 for use with a subsequent or next new biomass in the reactor 1.

In more detail, the reactor 1 includes at least one basket 2 with a solid cylinder and a perforated bottom 3 for holding a biomass 6. A shower head 4 sprays solvent 7 whether an initial lignin solvent or the circulation solvent described herein, and inside the basket 2 and onto biomass 6. The solvent 7 flows on, over or through the biomass until it exits an outlet 17 at the bottom 3 of the reactor as a circulation solvent 13. In one form, the solvent may not collect within the reactor 1, and may flow continuously through the reactor 1 unless the valve V1 is closed. It will be understood that the reactor may alternatively have other configurations to deliver the solvent to the biomass and through the reactor. Thus, the reactor may also have a mixer instead or in addition to the shower head so that the solvent is collected in the reactor and then mixed to facilitate chemical reaction between the solvent and biomass.

The initial lignin solvent, by one example, may include about a 50-50 (wt. %) of an organic lignin dissolving chemical. As described herein, the lignin dissolving chemical for the first initial lignin solvent may be fresh butanol, fresh butyl acetate, fresh furfural, or any combination thereof. For subsequent initial lignin solvents used each time a new biomass is placed in the reactor, the lignin dissolving chemical may be partially or entirely formed of butyl ester and/or organic furan obtained from a separated circulating solvent used on a previous run for a previously fractionated biomass. Alternatively, the lignin dissolving chemical in the initial lignin solvent may include a distilled bio-oil produced from fast pyrolysis of biomass or lignin produced as a result of an organosolv fractionation process that is rich in acetic acid and water (where the acetic acid may be used to form further butyl ester as described herein). Other alternatives are mentioned herein.

The initial lignin solvent may also have an additional acid including sulfuric acid or acetic acid or both to decrease the pH to about 1.2 to 1.8. The initial lignin solvent and biomass (or in other words liquid to solid) are provided in about a 15 to 1 ratio, and in one form, about a 5 to 1 ratio. Also, the reactor 1 is heated until the biomass reaches and maintains at least about 175°-180° C. but in one form, at least approximately 178° C., and a pressure above atmospheric such as generally about 80-120 PSI, about 90-110 PSI, but in one form, about 100 PSI. This causes the fractionation 208 of the lignin from the cellulose and other materials.

The circulation solvent 13, which may be in liquid form, and which is the resulting solution or material from spraying the solvent onto the biomass, flows through an outlet 17 of the reactor 1, and in one example, on the bottom of the reactor 1. The circulation solvent 13 is then placed back into contact with the biomass by one example, circulating the circulation solvent back to the inlet at the top of the reactor 1, via pump 5, and to the spray head 4 for recirculation over and through the biomass 6. This recycling or recirculation process is operated for the duration of the fractionation process, such as 25-35 minutes but in one form, 30 minutes, and while the reactor is under a certain temperature and pressure as described herein. Alternatively, the recirculation of the circulation solvent 13 may be for time periods less than the entire fractionation process or cooking time, and may be continuous or provided at intervals, for example.

This process allows the solvent to penetrate into the biomass, dissolve the lignin that can be separated from the biomass, and at the same time, produce some organic material that is added to the organic part of the circulating solvent 7 for both immediate recycling through the current biomass as well as later collection to be reused in an initial lignin solvent for fractionating a new biomass. Specifically, during the cooking process, lignin and lignin-based compounds within a biomass dissolve into the organic portion of the solvent. This frees the cellulose so that the biomass has relatively loose cellulosic fibers. In addition to lignin, the cooking process releases some of the hemicellulose as C5 sugar into an aqueous part of the solvent and converts some of the hemicellulose into acetic acid, furfural, and other organic compounds that are released into the organic part of the circulation solvent. These materials also may be in liquid form.

The recirculation of the circulation solvent, in one form, occurs without separating any of the material from the circulation solvent. Thus, the circulation solvent may contain at least organic materials or liquor, lignin, or lignin compounds, water, and sugar, which are all placed back into contact with the biomass at least one, and in one form many times. In one example, the recycling of the circulation solvent occurs without isolating and removing any particular type of material from the circulation solvent that is placed back into contact with the biomass. Another way to say this is that in one form, the recycling occurs without any substantial processing of the contents of the circulation solvent, such as distillation of materials.

The circulation and cooking is performed for a set period of time, as mentioned above, such as for approximately 30 minutes in one example, before the circulating solvent is delivered to the separation tank 9 for separating of the materials within the circulation solvent, and replacing the resulting pulp in the reactor 1 with a new biomass. The time period, as well as the flow rate of the circulating circulation solvent, is selected based on the type of biomass used and the time it takes to significantly break down the biomass and remove most of the available lignin from that particular biomass. Recirculation of the circulation solvent can continue until it is significantly saturated with lignin and is no longer able to extract lignin from the biomass.

Alternatively, a portion of the circulation solvent may be redirected away from the circulation loop for more immediate separation and processing while the remainder of the circulation solvent is being circulated over or through the biomass. In this case, as another option, fresh initial lignin solvent may be supplied to the reactor to replace the removed circulation solvent, and during the circulation or cooking period.

After the time period is complete, the initial lignin solvent 7 is fully transformed into the circulation solvent 13 which includes liquor enriched with the dissolved lignin and other organic material, lignin, generated chemicals, water, and remaining solvents as mentioned above. This final or resulting circulation solvent is then extracted into settling or separation tank 9 for separation 210.

The basket 2 that includes the remaining solids 6 which has now been transformed into a pulp including cellulose fibers 212 and some trapped liquid, are dumped into a centrifuge 8 that extracts some of the remaining liquid from the remaining solid.

The separated liquid from centrifuge 8 may be directed to the settling tank 9 through a flow path 14 for one example, or otherwise may be removed from the centrifuge and dumped into the separation tank 9. Inside the settling tank 9, the circulation solvent 13, in one example mainly in a liquid phase, separate into an organic layer 10, 214 that floats on top due to its density, and an aqueous layer 11, 216 that drops to the bottom of the separation tank 9. The remaining solid 6, 212 from the centrifuge 8 is filtered 218 before the cellulose or fiber based pulp is provided for saccharification 224 or acid hydrolysis.

Figure 4:
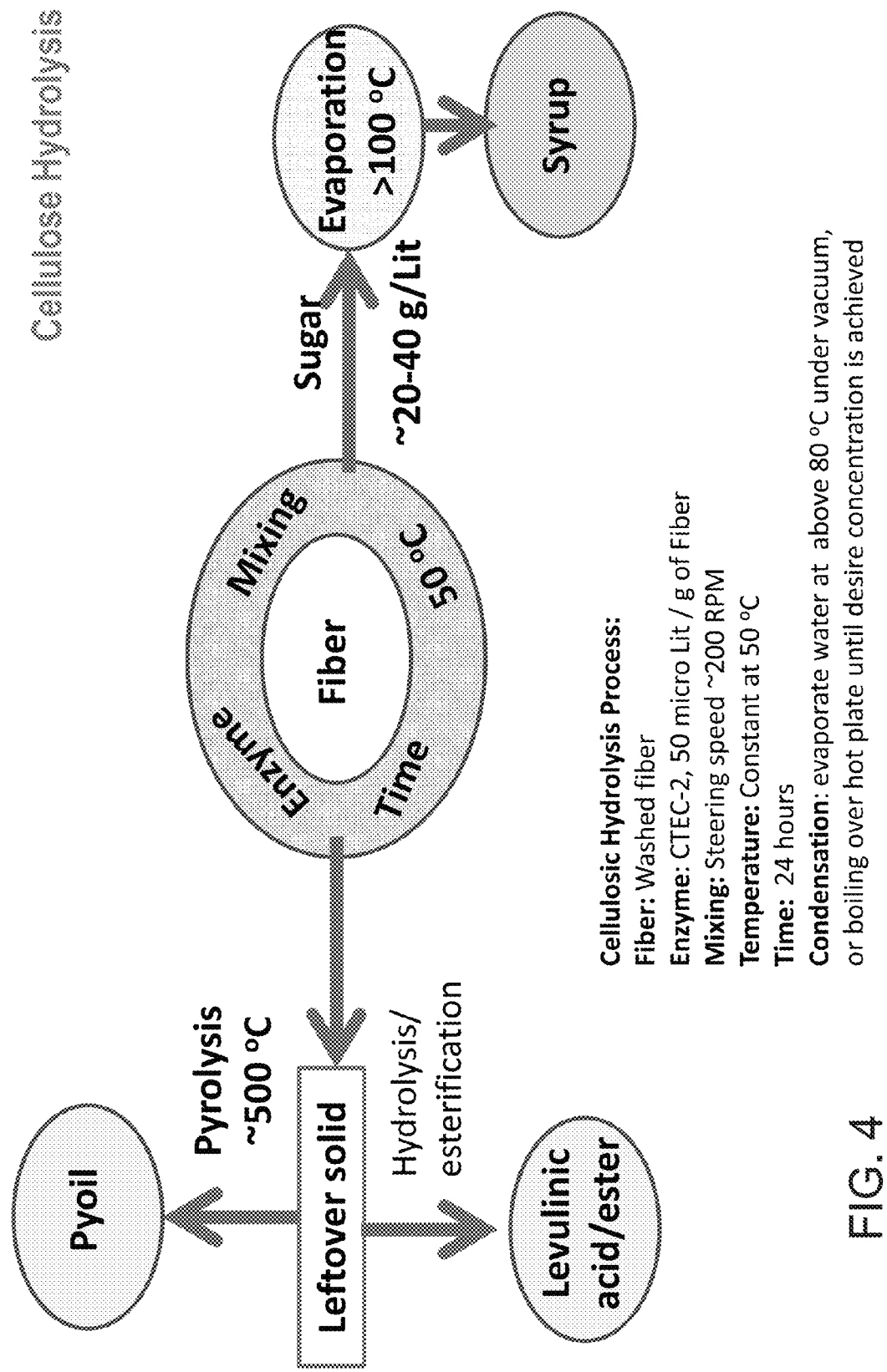
FIG. 4 is a process flow for cellulose hydrolysis.

Referring to FIGS. 2 and 4, by one approach, hydrolysis of the cellulose (from the pulp in fiber form in one example) includes first washing the fiber 220 before mixing the fiber with an enzyme 222 for saccharification 224, which in one form is CTEC-2, and at an approximately constant 50° C. to produce C6 sugar that can be submitted to an evaporation process. The enzyme-fiber mixture may be mixed at approximately 200 RPM inside a fermenter for about 24 hours. At the end of the hydrolysis process, the resulting sugar syrup is separated from leftover solids by filtration. The leftover solids may be submitted to a Fast Pyrolysis at about 500° C. to form Pyoil which may be used as bio-oil or converted into Levulinic ester, Butyl ester, and other chemicals thereafter. The separated sugar syrup is transferred into a fermenter while bacteria 226 may be added for fermentation 228 to form C6 sugar derivative products. If necessary, to evaporate water in the sugar-mixture, the heat is raised to about 80-110° C. under vacuum, or boiling over a hot plate, or by use of a flash evaporator, until a desired concentration is reached, and thereafter forms a syrup. The products from fermentation 228 then may be distilled 230 to separate products such as biofuels 232 or any other C6 sugar base products.

Referring again to FIG. 2, all or part of the aqueous layer 11, 216 is recycled 234 back into the system, in one form, into initial solvent tank 12 to be used as part of the initial lignin solvent 7 for a next new biomass. All or part of the organic layer 10, 214 also may be sent to a distillation system to separate 236 desirable chemicals 238 such as furans (including furfural), esters (including butyl acetate), ethers, and vanillin, and the lignin 240 from the remaining organic solvent 242 (also referred to as the solvent for recycle or simply solvent recycle).

The separated lignin 240 may be used as described herein, and in one alternative, the lignin may be further mixed with one or more polymers to form a portion of a polymer or plastic object, such as a toy for example, or may be used as a colorant in a plastic object. In one form, the plastic object may be about 3-7%, about 4-6%, or about 5% lignin. The lignin may be a colorant for poly lactic acid for example, and may be used in an injection mold or extruded. Other polymers are contemplated.

The entire organic solvent 242 may be placed back into the initial solvent tank 12, or it may be further distilled itself to include, or only include, butyl ester or organic furan or both for reuse in the initial lignin solvent 244. In the latter case when butyl ester or organic furan is to be reused, it may be obtained by sharing the same distillation process as that used for removing chemicals 238 from the system. The new initial lignin solvent 244 for a new biomass placed in the reactor 1, whether in a batch process or otherwise in a continuous process, may include fresh lignin solvent, such as added butanol, used to start the fractionation process and the remaining circulation solvent or portions of the circulation solvent, such as the butyl acetate and/or furfural, that were produced as a result of the fractionation process as explained above, separated, and then reused or recycled back into the initial solvent tank 12 to be used with the next new biomass.

As mentioned above, both the first initial lignin solvent and the subsequent initial solvents may have many different compositions for their lignin dissolving chemical including butanol, a butyl ester, or an organic furan, or any combination of two or three of these chemicals. In one form, both the first and subsequent initial solvents are mixtures of all three chemicals. In another form, the first initial solvent has butanol, and in one form only butanol, as the lignin dissolving chemical, while the subsequent initial solvents are solely a mixture of the three chemicals or the three chemicals mixed with others from the circulating solvent whether separated or not. In one form, the lignin dissolving chemical only includes these three chemicals, and in another form, the lignin dissolving chemical may include additional chemicals. By one approach, as mentioned above, the mixture in the dissolving chemical in the first and/or subsequent initial lignin solvents is generally or substantially maintained at approximately ⅓ equal parts by weight of butanol, butyl ester, and organic furan.

Figure 5:
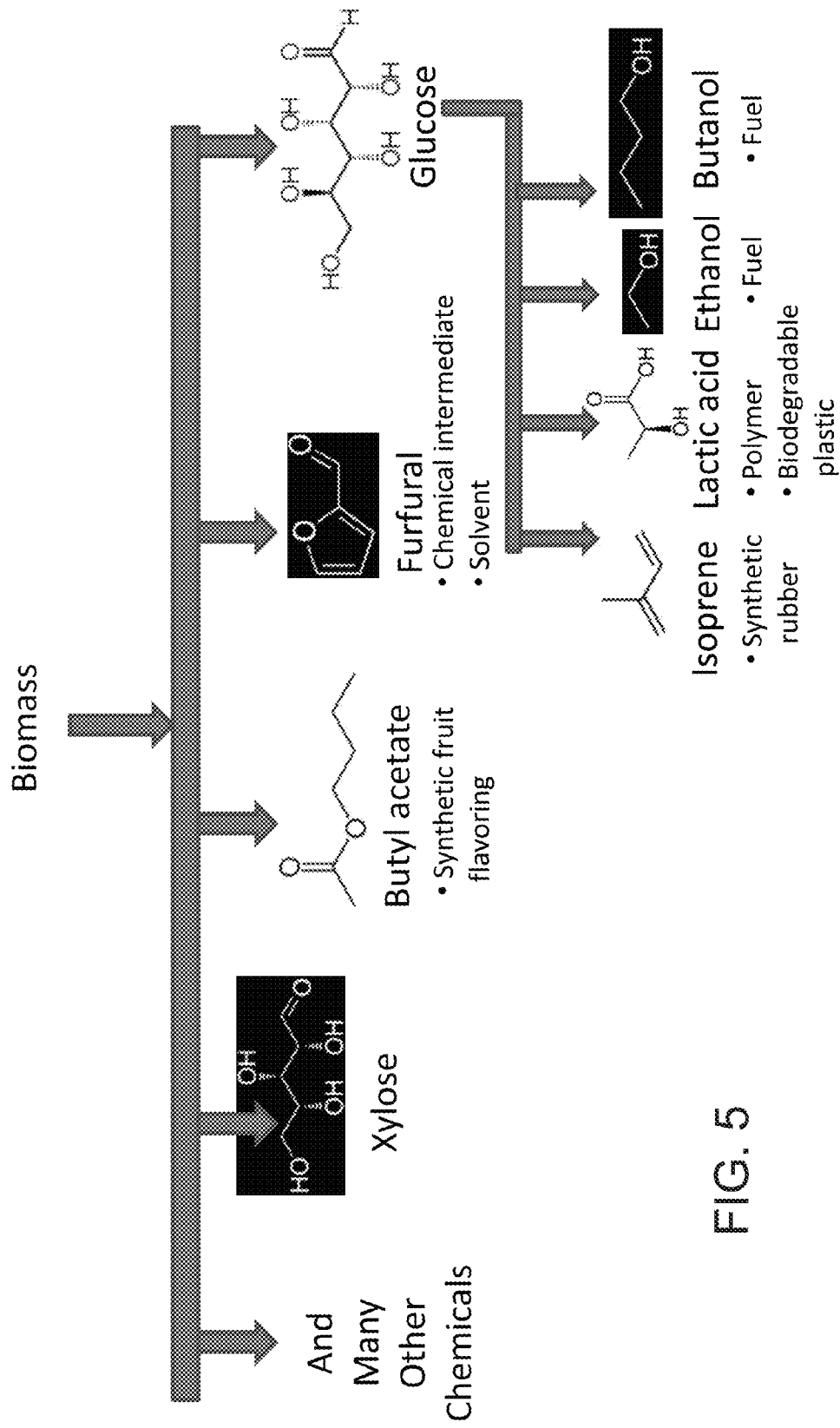
FIG. 5 is a schematic diagram showing some of the chemicals produced from the process described herein.

Referring now to FIG. 5, the following is a more detailed description of a number of products produced by the process described herein. In one example form, the basic four intermediary products produced by the process includes butyl acetate, furfural, glucose, and xylose, the structures of which are shown on FIG. 5. Butyl acetate may be processed further to manufacture synthetic fruit flavoring for example. Furfural is a chemical intermediate used to produce furfural alcohol for furan resins, and both the Butyl acetate and Furfural individually, together, or as a mixture with other lignin solvent organic chemicals, may be used as the lignin solvent. Other details of these two chemicals are as follows:

Butyl Acetate:

Other names: Butyl ethanoate, acetic acid, n-butyl ester.

Uses: petrochemicals, fuel additive and solvent.

Formula:

$$C6H12O2$$

Structure:

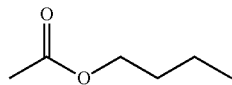

Furfural:

Other names: furan-2-carbaldehyde, furfural, furan-2-carboxaldehyde, fural, furfuraldehyde, 2-furaldehyde, and pyromucic aldehyde.

Uses: solvent, petrochemicals, pharmaceutical intermediates.

Formula:

Structure:

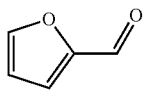

The process may also form glucose and xylose that may be further processed to produce isoprene used to make synthetic rubbers, lactic acid used to make polymers such as biodegradable plastics, and ethanol and butanol to be used as biofuels to name a few examples.

Other chemicals that may be made from the processes described herein include:

Vanillin:
Other names: 4-hydroxy-3-methoxybenzaldehyde, methyl vanillin, vanillic aldehyde
Uses: flavoring in foods, beverages, and pharmaceuticals.

Formula: $C_8H_8O_3$

Structure

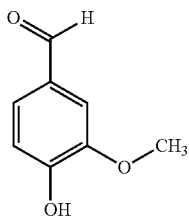

Levulinic Acid, Butyl Ester:
Other names: n-butyl levulinate; butyl levulinate; levulinic acid n-butyl ester; 4-ketopentanoic acid butyl ester; butyl laevulinate; n-butyl laevulinate; butyl 4-oxopentanoate; n-butyl 4-oxopentanoate.
Uses: petrochemical, fuel additive and solvent.

Formula:

Structure:

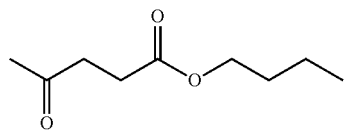

Butane, 1,1-dibutoxy:
Other names: butyraldehyde, dibutyl acetal; lageracetal; 1,1-dibutoxybutane.
Uses: fuel additive to increase octane number Formula:

Structure:

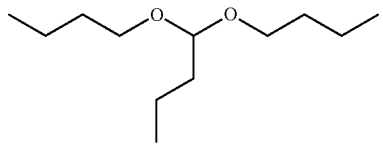

Dibutyl Ether:
Other names: butyl ether
Uses: Solvent for Grignard syntheses, technical solvent for fats, oils, organic acids, alkaloids, natural and synthetic resins extractant, constituent of catalysts for (co-) polymerizations, and for manufacturing of pesticides (e.g. Cyhexatin)

Formula:

Structure:

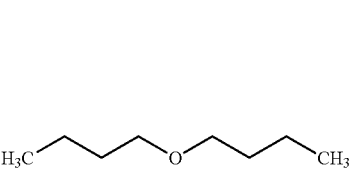

The chemical transformations that may be performed by using the process described herein include the following:

Butyl Acetate Formation:

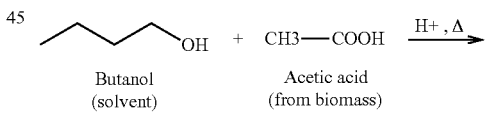

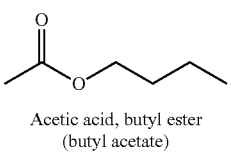

Acetic acid, butyl ester
(butyl acetate)

Levulinic Ester Formation:
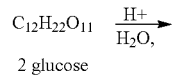
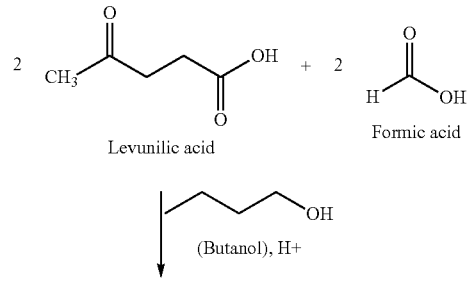
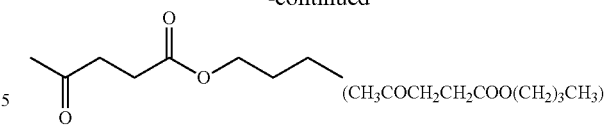
Levulinic acid butyl ester (Pentanoic acid, 4-oxo butyl ester)
Furfural Formation:
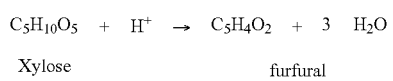
Vanillin Formation:
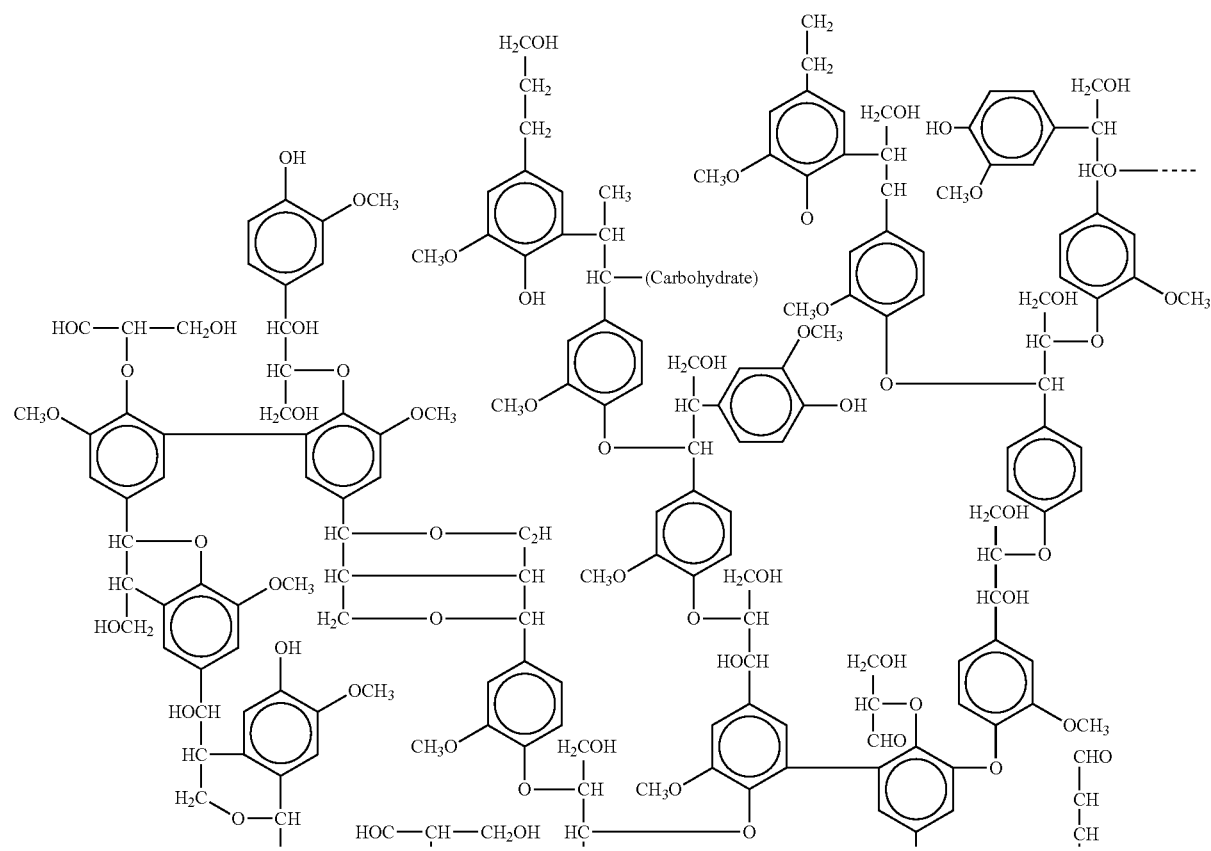

-continued

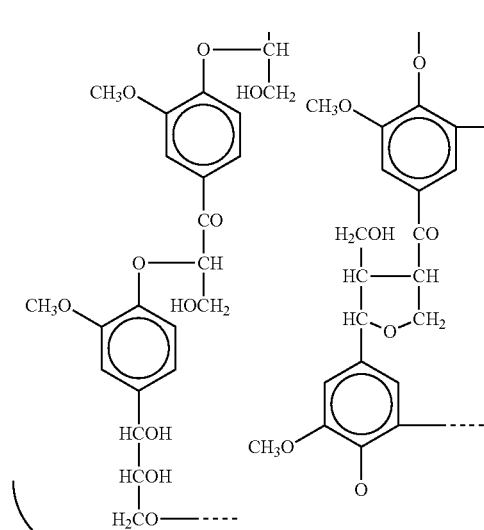
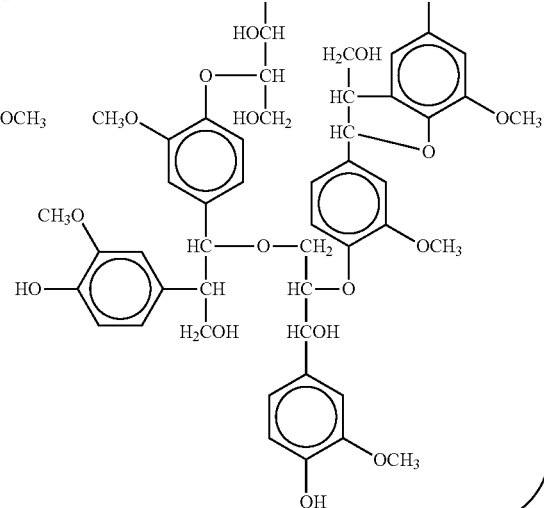

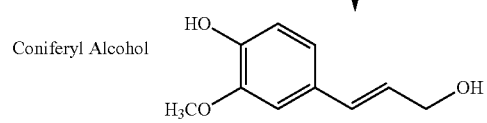

Coniferyl Alcohol

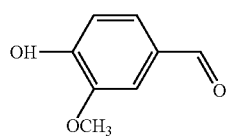

Vanillin

Butane, 1,1-dibutoxy:

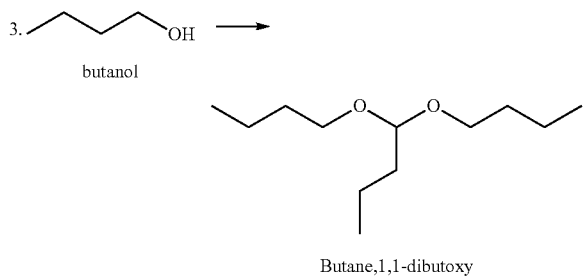

Butane,1,1-dibutoxy

Dibutyl Ether Formation:

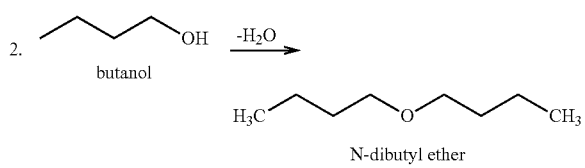

N-dibutyl ether

Figure 6:
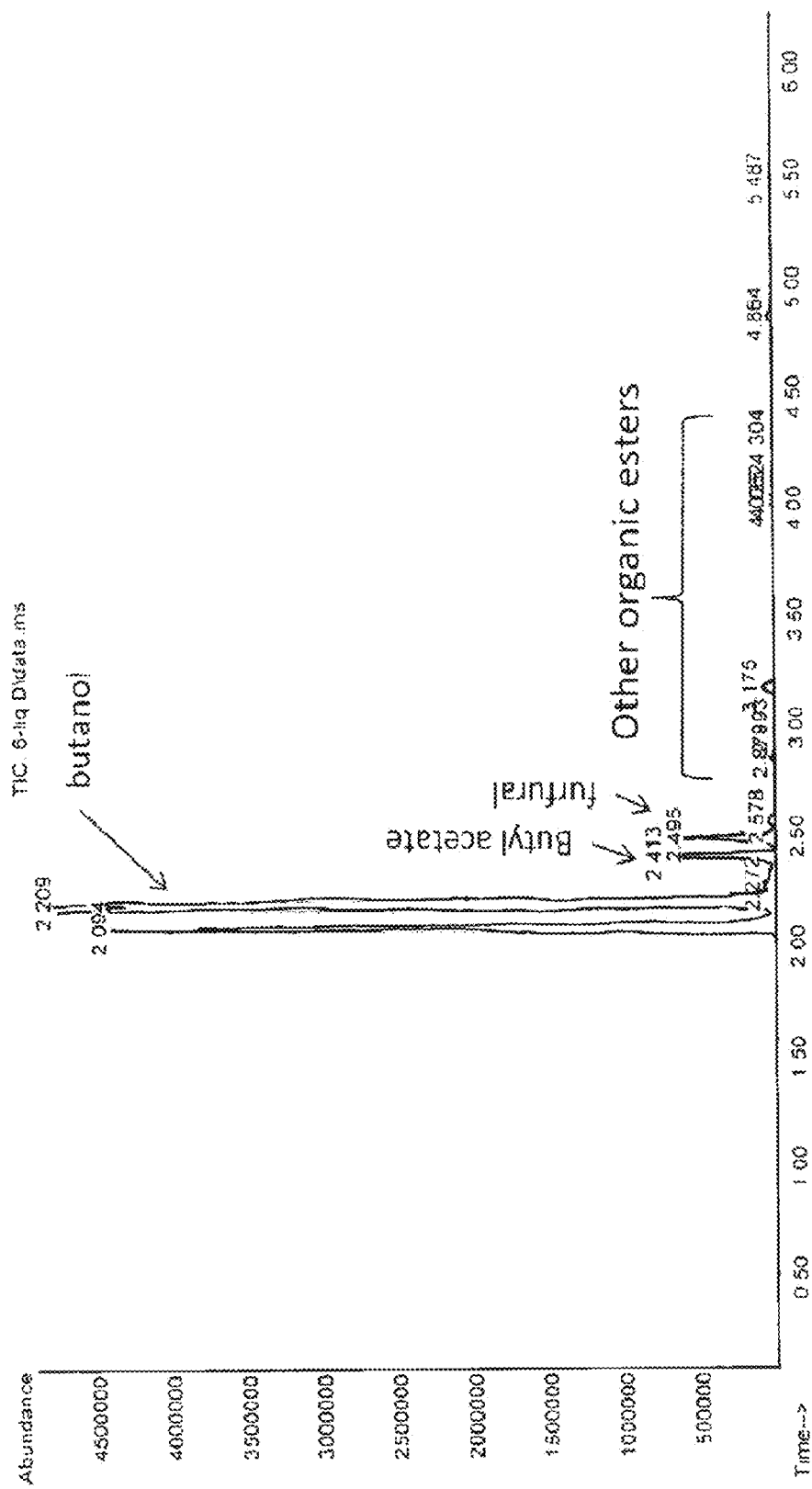
FIG. 6 is a gas chromatography-mass spectrometry (GCMS) graph showing organic chemicals produced from a process described herein.

Referring to FIG. 6, a gas chromatography, mass spectrometry (GCMS) graph of the organic materials produced as a result of a fractionation process as disclosed herein is provided using butanol as the lignin dissolving chemical in the initial lignin solvent. This corresponds to Sample WB6 shown below (table 3A-3B). This chart can be used to compare to the results using other types of lignin dissolving chemicals or while changing the parameters of the process as disclosed below.

For examples 1-12 described below, all of the experiments were performed in a laboratory with a batch reactor (mechanically stirred-250 mL stainless steel autoclave) that mixes the ingredients placed in the reactor such as Parr reactor model no. 4560 and 4570. The rpm used for mixing is noted below. This is different from the pilot reactor 1 that merely showers the solvent onto the biomass. Thus, while 30 mins. of digestion is sufficient for the Parr reactors, the shower reactor may use 60 to 90 min. of digestion for a more complete reaction. The mixing in the Parr reactors also assists with breaking down and disintegrating the semi-digested biomass during the process which enhances the fractionation process. On the other hand, in the shower reactor, the integrity of the biomass particles may remain the same during the process. Thus, the Parr reactors can break down the biomass more than the pilot plant with shower head. So, for any given biomass, the Parr reactor types can extract more chemicals and their availability may promote more secondary reactions. The experiments, however, still provide an idea of the type and proportion of chemicals that maybe produced with the shower plant reactor.

Example 1 provided immediately below was performed to show the changes and effects to the recycling of the non-treated circulation solvent over time. Examples 2-12 below show the effect of changing various parameters and chemicals in the fractionation process.

EXAMPLE 1

An experiment was performed to test the effect of the circulation on the chemicals in the circulation solvent. The chemicals for three approximated cycles were tested after passing through the reactor and biomass. The cycles were tested without removing any particular type of chemical from the circulation solvent during the circulation and without performing any substantial treatment to the circulation solvent except for passing the solvent through the biomass.

For experiment 1, 25 g lignocellulosic biomass (mixed agricultural wastes) was used at 48% solid content or 12 grams of oven dry biomass. Generally, the target liquid (initial lignin solvent) to oven dry solid biomass by weight is five to one, where the initial lignin solvent includes sulfuric acid and equal amounts (by weight) of water and lignin dissolving chemical such as butanol. Here, the chemicals in the initial lignin solvent were 17 g water (in addition to 13 grams water from the biomass for a total of 30 g), 30 g lignin dissolving chemical (butanol), 0.36 g sulfuric acid and biomass in the reactor. The autoclave was purged two times with Ar prior to being pressurized with the required gas and heated to the required temperature for each cycle or sample in the delignification process below. The autoclave temperature was measured by a type-K Omega thermocouple placed inside the reactor body. At the completion of the experiment (cycle), forced air and cold water were used to facilitate cooling. Once the reactor reached room temperature, the pulp and solvent were removed from the reactor and separated by gravity filtration. The pulp was squeezed by hand to yield additional solvent before it was subjected to water washing. The collected solvents were then used as the circulation solvent in the reactor to perform the next experiment. To evaluate the changes in liquor chemistry, three different experiments, samples, or cycles XY-F14, XY-F16, and XY-F18 were carried out while keeping everything else constant. The solvent for the first cycle was collected after circulating the solvent for 30 minutes. The next two cycles were immediately collected after running the solvent through the reactor for about 30 minutes each. All the cycles were performed at 178° C., at 100 PSI and Ar atmosphere. Table 1 below is the result of gas chromatography-mass spectrometry (GCMS) data analysis.

TABLE 1

| Peak | | F14 | F16 | F18 |
|---|---|---|---|---|
| 2.332 | Acetic acid | 2.64 | 3.81 | 3.87 |
| 2.414 | Butanol | 63.16 | 53 | 44 |
| 2.497 | Formic acid, butyl ester | 2.18 | 1.62 | 2.56 |
| 2.637 | Butyl acetate | 9.25 | 12.62 | 12.8 |
| 2.728 | Furfural | 10.9 | 14.99 | 17.16 |
| 2.802 | n-butyl ether | 0.51 | 0.49 | 0.88 |
| 3.115 | 2-furancarboxaldehyde, 5-methyl | 0.7 | 0.9 | 1.53 |
| 3.231 | Propanoic acid, 2-hydroxy-, butyl ester | 0 | 0 | 0.51 |
| 4.188 | 2-furancarboxaldehyde, 5-(hydroxymethyl) | 3.98 | 4.81 | 5.07 |
| 4.262 | Butane, 1,1-dibutoxy | 1.29 | 0.73 | 0.69 |

TABLE 1-continued

| Peak | | F14 | F16 | F18 |
|---|---|---|---|---|
| 4.304 | Pentanoic acid, 4-oxo-, butyl ester (levulinic acid, butyl ester) | 0 | 0.54 | 1.02 |
| 5.1 | Vanillin | 0.2 | 0.3 | 0.37 |
| 5.343 | Phenol, 2-methoxy-4-propyl (homovanillyl alcohol) | 0.58 | 0.3 | 0.27 |

Figure 7:
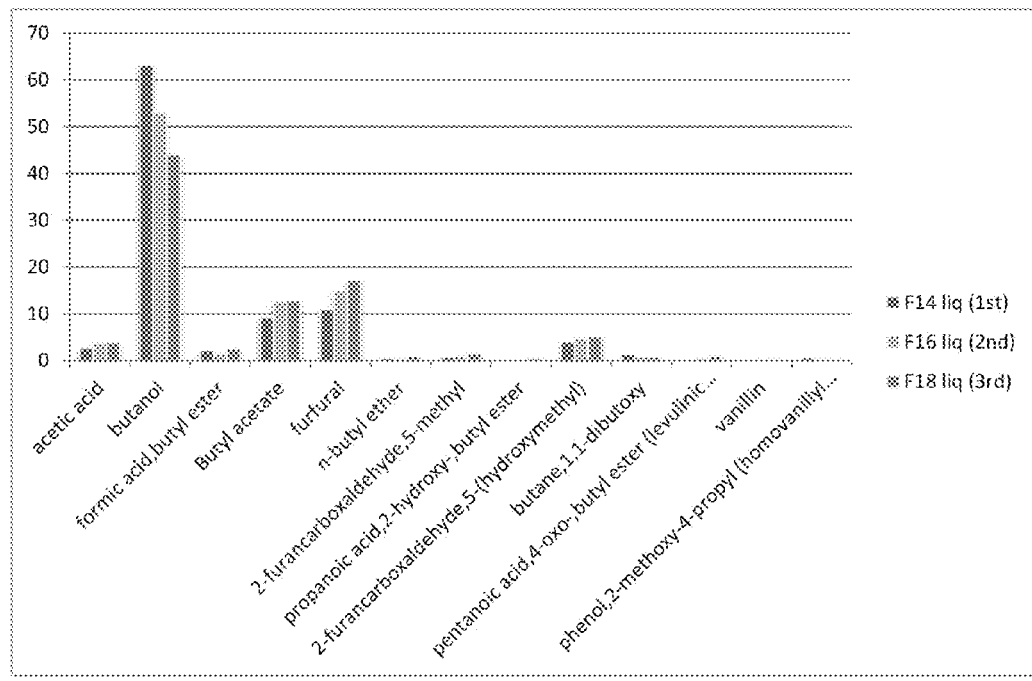
FIG. 7 is an example chart of chemicals that may be produced during a fractionation process while circulating a solvent.
Figure 8:
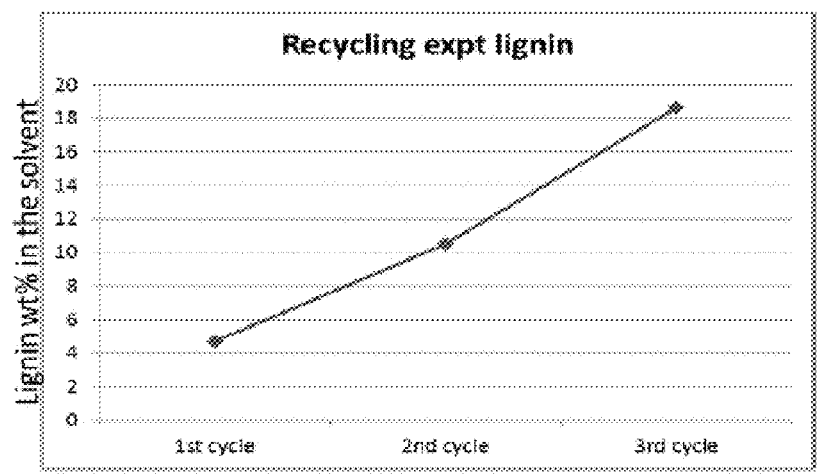
FIG. 8 is a graph showing the percentage of lignin in a circulating solvent over multiple cycles.

FIG. 7 is a graphic representation of the above table when butanol, used as the main lignin dissolving chemical in the initial lignin solvent, was removed from the data to magnify the other products' fluctuations. As the circulation solvent is recycled, it was observed that if butanol is in the system, it will be used to make other derivatives of the butanol, mostly butyl acetate. Also, the concentrations of acetic acid, furfural, and vanillin all increased over time during the recirculation. As shown on FIG. 8, the percentage of lignin content in the circulation solvent rises as the circulation solvent is recycled, and from cycle to cycle here at about 5%, then about 10%, and finally at about 19%. In one form, and as shown, the lignin content increases until the circulation solvent is saturated with lignin (around 22% or in another form, about 20% to about 24%) such that it requires distillation and removal of lignin before the next cycle. Thus, the lignin should be removed from the liquor after about three 30 minute periods of digestion or the lignin saturates the liquor and the solvent loses its capability of removing more lignin. As a result, in one form, all or part of the solvent is removed from the recycling process, distillated to remove the lignin, and then recirculated back into the refreshed solvent and into the system.

The increasing amount of lignin and other derivative chemicals corresponding to the order of the cycles also tends to confirm the production of butyl ester and furfural by starting with butanol, and show that the combination of butanol with butyl ester or furfural or both is a more efficient solvent than butanol alone.

Examples 2-17 are provided below modifying certain variables to determine the effect of the variable on the process. The data and observations are as follows.

EXAMPLE 2

Effect of Temperature

Experiments were performed in a batch reactor (mechanically stirred-250 mL stainless steel autoclave) using 25 g wood chips at 48% moisture content (12 g oven dry biomass and 13 grams of water). In Example 2, the initial lignin solvent included 17 g additional water and 30 g butanol (liquid to solid by wt=5; water:butanol=1:1 by wt), as well as 0.36 g sulfuric acid, and the biomass included wood chips added to the reactor. The autoclave was then purged two times with Ar prior to being pressurized with the required gas and heated to the required temperature for the delignification process. The autoclave temperature was measured by a type-K Omega thermocouple placed inside the reactor body. The initial lignin solvent was recycled through the reactor and on the biomass to form a circulation solvent and for a set period of time recited below. After the period of time, forced air and cold water were used to facilitate cooling. Once the reactor reached room temperature, the pulp and solvent were removed from the reactor and separated by gravity filtration. The pulp was squeezed by hand to yield additional solvent before it was subjected to water washing. The collected solvents were then allowed to settle down in a separating tank or funnel to separate the aqueous and liquor fractions. One gram of liquor was then dried for an hour at approximately 100° C. to evaluate the amount of lignin extracted from the wood chips.

To evaluate the effect of temperature on the lignin extraction process three different experiments with test numbers WA1, WB1, and WB5 were respectively carried out at 160° C., 178° C., and 225° C. All the experiments (or more specifically the circulation of the solvent) were carried out at 100 PSI initial Ar pressure for 30 minutes. Table 2A lists the resulting lignin and pulp yield. Table 2B presents the effects of temperature on lignin and pulp production. The significance here is that at 225° C., zero pulp was produced and created a state of simultaneous fractionation and hydrolysis.

TABLE 2A

Effect of Temperature

| Sample | Temperature (° C.) | lignin % | pulp yield % |
|---|---|---|---|
| WA1 | 160 | 6.63 | 64.8 |
| WB1 | 178 | 11.33 | 55.38 |
| WB5 | 225 | 10.64 | 0 |

TABLE 2B

Effect of Temperature on production of chemicals

| Test Conditions, Test Number >>> | WA1 | WB1 | WB5 | |
|---|---|---|---|---|
| Temperature | 160 | 178 | 225 | Variable |
| Time | 30 min | 30 min | 30 min | Constant |
| pressure (Pi) | 100 PSI | 100 PSI | 100 PSI | Constant |
| solvent butanol:water (1:1 by wt) | 1:1 | 1:1 | 1:1 | Constant |
| Acid | H2SO4 | H2SO4 | H2SO4 | Constant |
| feedstock, woodchips | W | W | W | Constant |
| gas/oxidants | Ar | Ar | Ar | Constant |
| solvent to solid ratio | 5 | 5 | 5 | Constant |

| Data | WA1, g/L | g/L WB1 | g/L WB5 | |
|---|---|---|---|---|
| acetic acid | 1.71 | 6.86 | 7.97 | |
| Butanol | 234.40 | 372.80 | 351.00 | Base |
| formic acid, butyl ester | 0.00 | 0.00 | 12.14 | ** |
| Butyl acetate | 15.13 | 19.79 | 27.83 | ** |
| Furfural | 12.42 | 21.77 | 12.89 | * |
| n-butyl ether | 0.94 | 1.08 | 16.92 | ** |
| Propanoic acid, 1-methylpropyl ester | | | | |
| Propanoic acid, butyl ester | | | | |
| 2-furancarboxaldehyde, 5-methyl | 0.69 | 1.42 | 2.06 | ** |
| Butanoic acid, butyl ester | | | | |
| Propanoic acid, 2-hydroxy-, butyl ester | 0.50 | 1.42 | 3.19 | ** |
| Oxirane, pentyl | | | | |
| Morpholine | 1.21 | 1.21 | 0.00 | |
| Butane, 1-(ethenyloxy) | | | | |
| Phenol, 2-methoxy | 0.33 | 0.65 | 0.00 | |
| 2-furancarboxaldehyde, 5-(hydroxymethyl) | 0.88 | 2.11 | 1.12 | * |
| Butane, 1,1-dibutoxy | 0.36 | 0.60 | 0.00 | |
| Pentanoic acid, 4-oxo-, butyl ester (levulinic acid, butyl ester) | 0.00 | 0.00 | 19.68 | ** |
| 5-acetoxymethyl-2-furaldehyde | 0.00 | 0.00 | 0.00 | |

TABLE 2B-continued

Effect of Temperature on production of chemicals

| Test Conditions, Test Number >>> | WA1 | WB1 | WB5 | |
|---|---|---|---|---|
| Vanillin | 0.69 | 1.16 | 7.08 | ** |
| Phenol, 2-methoxy-4-propyl (homovanillyl alcohol) | 0.00 | 0.00 | 0.00 | |
| 2-butenoic acid, hexyl ester | 0.00 | 0.00 | 0.56 | |
| Total grams/liter (g/l) chemicals in liquor | 269.26 | 430.88 | 462.42 | ** |
| Lignin as % of total liquor | 6.63% | 11.33% | 10.64% | |
| water 19% theoretical value | 19.00% | 19.00% | 19.00% | |

** represents a significant change in production for all tables herein unless otherwise noted.
* represents major fluctuation in data unless otherwise noted.

Base refers to the base, initial lignin dissolving material in the solvent for this test, which was butanol, and as a result GCMS shows a large spike for butanol. To better understand the results, the base was typically removed to avoid over-shadowing or distorting all other data results.

The following observations are made:

1. At higher temperature, pulp starts to hydrolyze and converts to other chemicals (for example at 225° C., almost all pulp was hydrolyzed and only solid char was observed at the end).
2. At temperatures above 200° C., the cellulose is hydrolyzed to C6 sugar (glucose) and the C6 sugar subsequently converted to levulinic acid (pentanoic acid, 4-oxo). The produced levulinic acid in situ reacted with butanol to produce levulinic acid, butyl ester.
3. The higher temperature also favors condensation of two butanol molecules to produce n-dibutyl ether.
4. The higher temperature favors the formation of acetic acid.
5. At higher temperature, less sugar in the aqueous layer is observed such that most of the C5 sugar is converted to other chemicals.
6. At 225° C., the process presents degradation of some lignin to other chemicals such as vanillin (dip fragmentation of lignin).
7. More Furfural is produced at 178° C., compared to 225° C. At a higher temperature, C5 sugars favor formation of furan and propanoic acids.
8. The amount of lignin extracted at 160° C. is less than the amount extracted at 178° C., and the pulp obtained from the 160° C. fractionation produces less sugar yield which indicates a greater amount of lignin remaining in the pulp. As a result of a greater amount of lignin left in the resulting pulp, the enzymes cannot hydrolyze the pulp efficiently to sugar.
9. At 225° C., about 95% of the total biomass is converted to chemicals and lignin, and the remaining biomass material is char.

Figure 9:
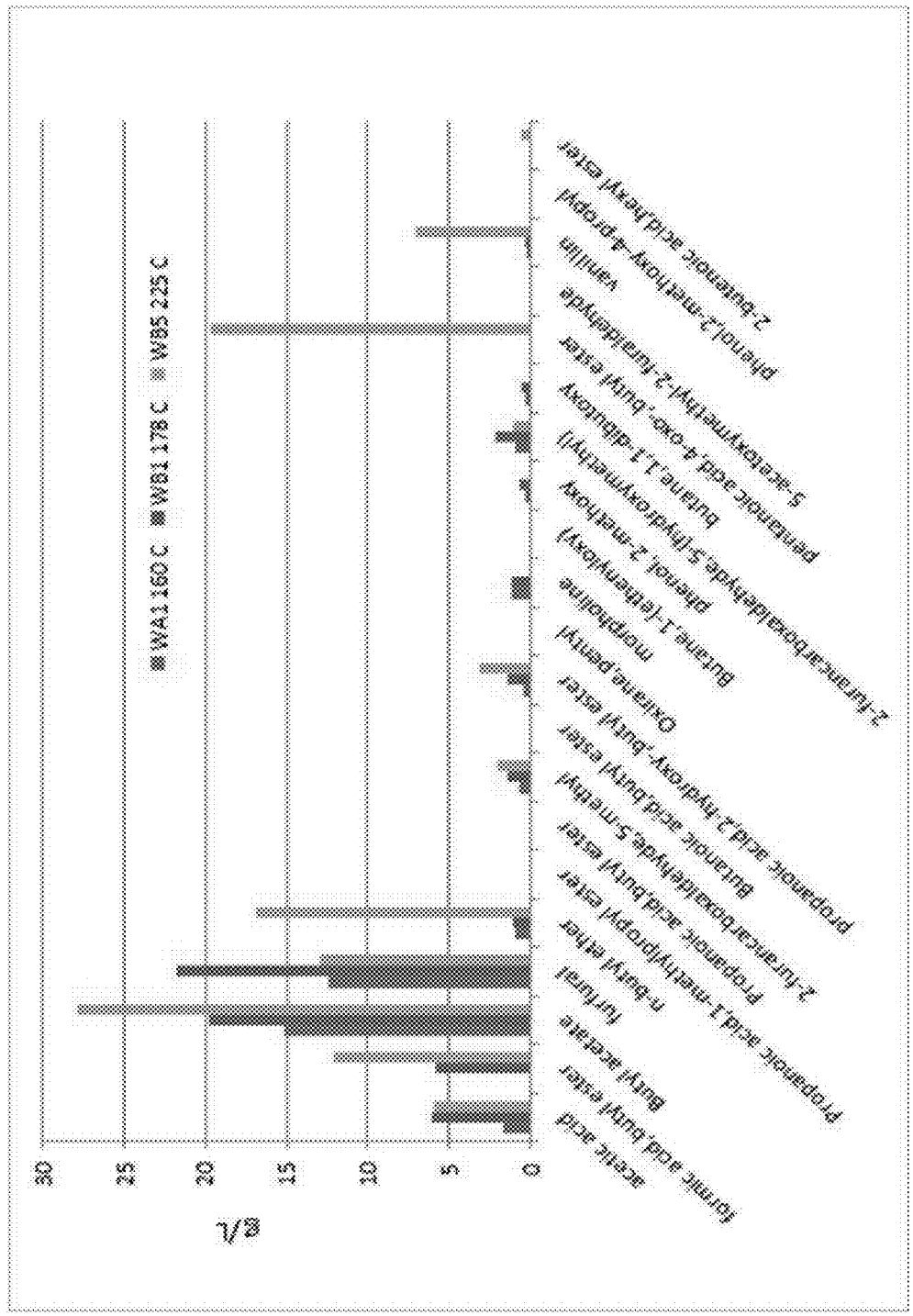
FIG. 9 is an example chart of chemicals that may be produced during a fractionation process and in amounts depending on temperature.

Referring to FIG. 9, a chart presents the distribution of chemicals produced from the process described above for Example 2 and due to changes in process temperature. The chemicals were measured in grams per Liter.

EXAMPLE 3

Effect of Pressure

The same solvent, biomass, and general parameters as in Example 2 were used for Example 3 except for the variation in pressure. Specifically, to evaluate the effect of pressure on the lignin extraction process, three different experiments were carried out at initial Ar pressure of 0 PSI (WB4), 100 PSI (WB1 already described above), and 200 PSI (WB6). All the experiments were carried out at 178° C. for 30 minutes. Table 3A lists the resulting lignin and pulp yield. Table 3B lists the parameters used as well as the specific chemicals produced for samples WB1, repeated from Table 2B, WB4, and WB6.

TABLE 3A

Effect of Pressure

| Sample | Pressure | Lignin % | Pulp yield % |
|---|---|---|---|
| WB4 | 0 | 11.85 | 47.82 |
| WB1 | 100 | 11.33 | 55.38 |
| WB6 | 200 | 12.56 | 31.86 |

TABLE 3B

Effect of Pressure

| Test Conditions, Test Number >>> | WB1 | WB4 | WB6 | |
|---|---|---|---|---|
| Temperature | 178 | 178 | 178 | Constant |
| Time | 30 min | 30 min | 30 min | Constant |
| pressure (Pi) | 100 psi | 0 psi | 200 psi | Variable |
| Solvent, butanol:water (1:1 by wt) | 1:1 | 1:1 | 1:1 | Constant |
| Acid | H2SO4 | H2SO4 | H2SO4 | Constant |
| Feedstock | wood-chips | wood-chips | wood-chips | Constant |
| Gas/oxidants | Ar | Ar | Ar | Constant |
| Solvent to solid ratio | 5 | 5 | 5 | Constant |

| Products Data | g/L WB1 | g/L WB1 | g/L WB6 | |
|---|---|---|---|---|
| Acetic acid | 8.63 | 6.86 | 9.08 | * |
| Butanol | 365.63 | 372.80 | 373.75 | Base |
| Formic acid, butyl ester | 6.68 | 0.00 | 11.29 | ** |
| Butyl acetate | 30.80 | 19.79 | 29.83 | * |
| Furfural | 26.62 | 21.77 | 27.52 | * |
| n-butyl ether | 1.77 | 1.08 | 4.90 | ** |
| Propanoic acid, 1-methylpropyl ester | 0.00 | 0.00 | 0.00 | |
| Propanoic acid, butyl ester | 0.00 | 0.00 | 0.00 | |
| 2-furancarboxaldehyde, 5-methyl | 1.64 | 1.42 | 1.73 | |
| Butanoic acid, butyl ester | 0.00 | 0.00 | 0.00 | |
| Propanoic acid, 2-hydroxy-, butyl ester | 1.54 | 1.42 | 1.20 | |
| Oxirane, pentyl | 0.00 | 0.00 | 0.00 | |
| Morpholine | 1.18 | 1.21 | 1.06 | |
| Butane, 1-(ethenyloxy) | 0.00 | 0.00 | 0.00 | |
| Phenol, 2-methoxy | 0.36 | 0.65 | 0.00 | |
| 2-furancarboxaldehyde, 5-(hydroxymethyl) | 3.41 | 2.11 | 6.05 | ** |
| Butane, 1,1-dibutoxy | 0.86 | 0.60 | 0.00 | |
| Pentanoic acid, 4-oxo-, butyl ester (levulinic acid, butyl ester) | 0.59 | 0.00 | 4.56 | ** |
| 5-acetoxymethyl-2-furaldehyde | 0.00 | 0.00 | 0.00 | |
| Vanillin | 1.86 | 1.16 | 7.88 | ** |
| Phenol, 2-methoxy-4-propyl (homovanillyl alcohol) | 0.86 | 0.00 | 0.53 | |
| 2-butenoic acid, hexyl ester | 0.55 | 0.00 | 0.48 | |
| grams/liter (g/l) | 452.98 | 430.88 | 479.84 | |
| Lignin as % of total liquor | 11.80% | 11.33% | 12.56% | |
| Water 17.5% (close to theoretical value) | 17.50% | 17.50% | 17.50% | |

The following observations are made:
1. The fractionation and delignification process can be done at any initial pressure. Thus, regardless of pressure, we have been able to produce various chemicals although the productivity level changes.
2. Pressure changes production of the formic acid/butyl ester. Although there was no formic acid at 100 PSI, but, at 200 PSI, we were able to produce a significant amount of formic acid with all other conditions kept constant.
3. Higher pressure produces more n-butyl ether. Thus, for example, at 200 PSI, we were able to produce about three times more butyl acetate than at zero or 100 PSI when all other conditions were kept constant.
4. Higher pressure produces more 2-furancarboxaldehyde, 5-(hydroxymethyl). Thus, for example, at 200 PSI, we were able to produce about twice as much 2-furancarboxaldehyde, 5-(hydroxymethyl) than at lower pressures when all other conditions were kept constant.
5. Higher pressure produces more pentanoic acid, 4-oxo-, butyl ester (levulinic acid, butyl ester). For example, at 200 PSI, we were able to produce some of this chemical. However, at 100 PSI, either we produced none or an undetectable amount using GCMS, and when all other conditions were kept constant.
6. Higher pressure produces more vanillin. For example, at 200 PSI, we were able to produce about 85% more vanillin than at 100 PSI when all other conditions were kept constant.

Figure 10:
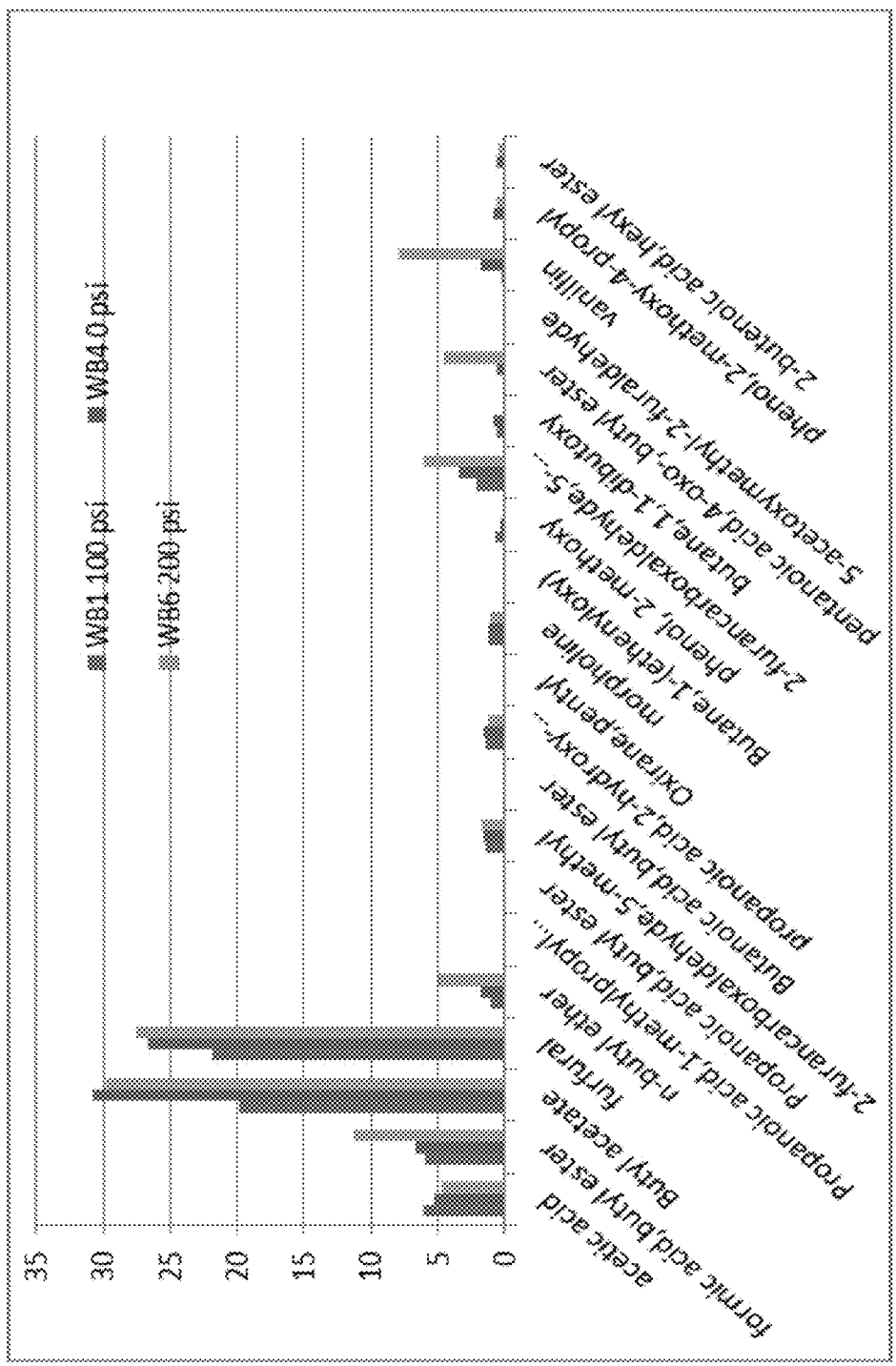
FIG. 10 is a chart of chemicals that may be produced during a fractionation process and in amounts depending on pressure.

Referring to FIG. 10, a chart presents the distribution of chemicals produced from the process described above and corresponding to the data above for Example 3 and due to changes in process pressure. The chemicals were measured in g/L.

Figure 11:
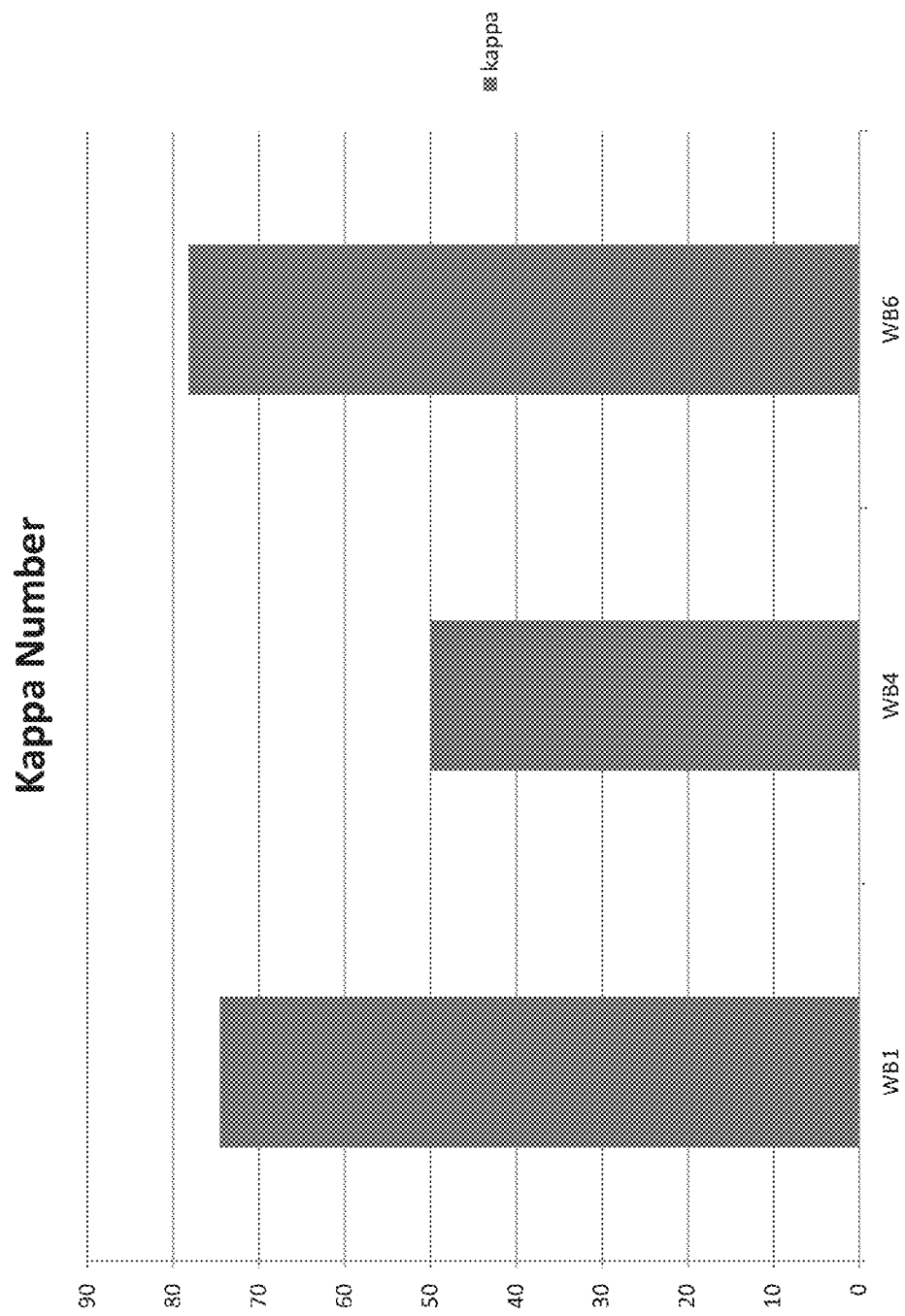
FIG. 11 is a chart showing a few examples of the Kappa Number reached for different conditions.

Referring to FIG. 11, a chart is provided that indicates the Kappa number for three different samples, WB1 at 100 PSI, WB4 at 0 PSI, and WB6 at 200 PSI. The Kappa number can be used to monitor the effectiveness of the lignin-extraction phase of a pulping process as here, and it is approximately proportional to the residual lignin content of the pulp. The Kappa number is based on ISO 302:2004 and gives a Kappa number in the range of 1-100. The Kappa number is a measurement of standard potassium permanganate solution that the pulp will consume. The measurement is inflated by the presence of hexenuronic acids in the pulp. These compounds are formed during the chemical pulping process, from the hemicelluloses. The Kappa number estimates the amount of chemicals required during bleaching of wood pulp to obtain a pulp with a given degree of whiteness. Since the amount of bleach needed is related to the lignin content of the pulp, this indicates the lignin content remaining in the pulp.

The chart shows that sample WB1 (100 PSI) has a Kappa number of about 75, while WB4 (0 PSI) is at about 50, and WB6 (200 PSI) is at about 78. This tends to show that the amount of lignin extracted is effected by pressure, where the greater the pressure, the more lignin may be extracted from the pulp or biomass.

EXAMPLE 4

Effect of Time

The same solvent, biomass, and general parameters as in Example 2 were used for Example 3 except for the variation in time. Specifically, to evaluate the effect of time on the lignin extraction process three different experiments were carried out at time 10 min, 30 min, and 60 min. All the experiments were carried out at 178° C., 100 PSI Ar. Table 4A lists the resulting lignin and pulp yield for various process times. Table 4B lists the parameters used as well as the specific chemicals produced for samples WB1 (30 min.), repeated from Table 2B, WB2 (60 min.), and WB3 (10 min.).

TABLE 4A

Effect of Process Duration Time

| Sample | Time | Lignin % | Pulp yield % |
|--------|------|----------|--------------|
| WB3    | 10   | 11.03    | 48.64        |
| WB1    | 30   | 11.33    | 55.38        |
| WB2    | 60   | 11.15    | 42.86        |

TABLE 4B

Effects of Process Duration Time (30, 60 min)

| Test Conditions, Test Number >>> | WB3 | WB1 | WB2 | |
|---|---|---|---|---|
| Temperature | 178 | 178 | 178 | Constant |
| Time | 10 min | 30 min | 60 min | Variable |
| Pressure (Pi) | 100 psi | 100 psi | 100 psi | Constant |
| Solvent butanol:water (1:1 by wt) | 1:1 | 1:1 | 1:1 | Constant |
| Acid | H2SO4 | H2SO4 | H2SO4 | Constant |
| Feedstock, woodchips | woodchips | woodchips | woodchips | Constant |
| Gas/oxidants | Ar | Ar | Ar | Constant |
| Solvent to solid ratio | 5 | 5 | 5 | Constant |
| Data | g/L WB3 | g/L WB1 | g/L WB2 | |
| Acetic acid | 7.88 | 6.86 | 5.31 | |
| Butanol | 385.13 | 372.80 | 339.60 | Base |
| Formic acid, butyl ester | 0.00 | 0.00 | 6.67 | ** |
| Butyl acetate | 28.85 | 19.79 | 28.65 | * |
| Furfural | 26.99 | 21.77 | 23.72 | |
| n-butyl ether | 1.86 | 1.08 | 2.42 | ** |
| Propanoic acid, 1-methylpropyl ester | 0.00 | 0.00 | 0.00 | |
| Propanoic acid, butyl ester | 0.00 | 0.00 | 0.00 | |
| 2-furancarboxaldehyde, 5-methyl | 1.44 | 1.42 | 1.49 | |
| Butanoic acid, butyl ester | 0.00 | 0.00 | 0.00 | |
| Propanoic acid, 2-hydroxy-, butyl ester | 1.21 | 1.42 | 1.74 | ** |
| Oxirane, pentyl | 0.00 | 0.00 | 0.00 | |
| Morpholine | 2.04 | 1.21 | 0.81 | |
| Butane, 1-(ethenyloxy) | 0.00 | 0.00 | 0.00 | |
| Phenol, 2-methoxy | 0.00 | 0.65 | 0.47 | |
| 2-furancarboxaldehyde, 5-(hydroxymethyl) | 2.83 | 2.11 | 4.72 | ** |
| Butane, 1,1-dibutoxy | 1.53 | 0.60 | 1.53 | * |
| Pentanoic acid, 4-oxo-, butyl ester (levulinic acid, butyl ester) | 0.00 | 0.00 | 1.28 | ** |
| 5-acetoxymethyl-2-furaldehyde | 0.00 | 0.00 | 0.00 | |
| Vanillin | 1.76 | 1.16 | 4.34 | ** |
| Phenol, 2-methoxy-4-propyl (homovanillyl alcohol) | 0.74 | 0.00 | 0.77 | |
| 2-butenoic acid, hexyl ester | 0.00 | 0.00 | 0.72 | |
| g/l>>>>>> | 462.26 | 430.88 | 424.22 | ** |
| Lignin as % of total liquor | 11.03% | 11.33% | 11.15% | |
| water 17.5% (close to theoretical value) | 17.50% | 17.50% | 17.50% | |

The following observations are made:

1. Acetic acid, butanol concentrations, and morpholine decrease with increasing time periods.
2. n-butyl ether concentration increases with time.
3. The amount of propanoic acid, 2-hydroxy-, butyl ester also increases with time.
4. Increase in process time will cause an increase in production of propanoic acid, 2-hydroxy-, butyl ester
5. Production of vanillinis increases with time.
6. Lignin extraction and sugar yield remains almost the same despite increasing time.
7. The process may produce an initial large amount of butyl acetate at 10 minutes that is broken down into other chemicals in secondary reactions upon further recycling.

EXAMPLES 5

Butyl Acetate as Organic Solvent

The basic process is the same as that of Example 2 above except here the solvent was varied, and includes 17 g water, 30 g of a main chemical (liquid to solid by wt=5; water:main chemical=1:1 by wt), and 0.36 g sulfuric acid, where the main chemical is butanol (Sample WB1 repeated here from Example 2 for comparison), butyl acetate (Sample WB10), furfural (Sample F), or butanol based distilled bio-oil (Sample WB17—this is an aqueous part of bio oil derived from biomass pyrolysis process as part of the solvent), Table 5 lists the data for all three Examples as well as sample WB1 for comparison to butanol from Example 2.

For Sample WB10, the experiment was carried out at 178° C., 100 PSI Ar for 30 min and 512 rpm as indicated below. When using butyl acetate (Sample WB10) in the solvent, 7.73% lignin was extracted by this process, and 56.67% pulp yield was obtained. Table 5 shows the detail of the parameters and chemicals produced.

TABLE 5

Effect of Solvent Type: Application of various organic solvents such as butanol, butyl acetate, furfural, bio-oil.

| Test Conditions, Test Number >>> | WB1 | WB10 | F | WB17 | |
|---|---|---|---|---|---|
| Temperature | 178 | 178 | 178 | 178 | Constant |
| Time (min) | 30 | 30 | 30 | 30 | Constant |
| Pressure (PSI) | 100 | 100 | 100 | 100 | Constant |
| Solvent mixture (1:1 by wt) | butanol: water | butyl acetate: water | furfural: water | butanol: bio-oil distilled | Variable |
| Acid | H2SO4 | H2SO4 | H2SO4 | H2SO4 | Constant |
| Feedstock, woodchips | W | W | W | W | Constant |
| Gas/oxidants | Ar | Ar | Ar | Ar | Constant |
| Solvent to solid ratio | 5 | 5 | 5 | 5 | Constant |
| Data | g/L | g/L | g/L | g/L | |
| Acetic acid | 6.86 | 132.75 | 3.47 | 2.18 | |
| Butanol | 372.80 | 284.00 | 0.00 | 70.06 | Base |
| Formic acid, butyl ester | 0.00 | 4.00 | 0.77 | 2.08 | |
| Butyl acetate | 19.79 | 399.37 | 0.27 | 15.12 | |
| Furfural | 21.77 | 37.36 | 423.00 | 5.11 | Base |
| n-butyl ether | 1.08 | 2.43 | 0.00 | 0.38 | |
| Propanoic acid, 1-methylpropyl ester | 0.00 | 0.00 | 0.00 | 0.00 | |
| Propanoic acid, butyl ester | 0.00 | 0.00 | 0.00 | 0.36 | |
| 2-furancarboxaldehyde, 5-methyl | 1.42 | 1.48 | 5.50 | 0.49 | |
| Butanoic acid, butyl ester | 0.00 | 0.00 | 0.00 | 0.00 | |
| Propanoic acid, 2-hydroxy-, butyl ester | 1.42 | 0.26 | 0.00 | 0.41 | |
| Oxirane, pentyl | 0.00 | 0.00 | 0.00 | 0.00 | |
| Morpholine | 1.21 | 0.00 | 0.00 | 0.25 | |
| Butane, 1-(ethenyloxy) | 0.00 | 0.00 | 0.00 | 0.00 | |
| Phenol, 2-methoxy | 0.65 | 0.00 | 0.32 | 0.28 | |
| 2-furancarboxaldehyde, 5-(hydroxymethyl) | 2.11 | 4.34 | 4.01 | 0.72 | |
| Butane, 1,1-dibutoxy | 0.60 | 0.00 | 0.00 | 0.40 | |
| Pentanoic acid, 4-oxo-, butyl ester (levulinic acid, butyl ester) | 0.00 | 0.96 | 0.00 | 0.00 | |
| 5-acetoxymethyl-2-furaldehyde | 0.00 | 0.78 | 0.00 | 0.00 | |
| Vanillin | 1.16 | 1.04 | 0.23 | 0.52 | |
| Phenol, 2-methoxy-4-propyl (homovanillyl alcohol) | 0.00 | 0.00 | 0.00 | 0.22 | |
| 2-butenoic acid, hexyl ester | 0.00 | 0.00 | 0.00 | 0.11 | |
| grams/liter (g/l) >>>>>> | 430.88 | 868.77 | 437.57 | 98.69 | |
| Lignin as % of total liquor | 11.33% | 7.73% | 13.23% | 10.85% | |
| Water 17.5% (close to theoretical value) | 17.50% | 17.50% | 17.50% | 17.50% | |

Sample WB10

The following observations are made:
1. Acetic acid produced from the biomass feedstock (by any method such as pyrolysis) can be used as a reactant to produce butyl acetate and other chemicals.
2. Butyl acetate can be used as a solvent for delignification of biomass.
3. Since butyl acetate is produced during the fractionation process, butyl acetate is a self-sustaining solvent.
4. Application of butyl acetate as the solvent produces more 2-furancarboxaldehyde, 5-(hydroxymethyl) than that produced when using butanol as a solvent.
5. Application of butyl acetate as the solvent produces more furfural than that produced when using butanol.

During the experiments, recycling of the butanol was very difficult, and practically impossible. As soon as the butanol passed through the reactor, pure butanol no longer existed. Instead, organic materials were produced that were all lignin solvents that then broke down the biomass. Among them, we noticed furfural and butyl acetate were the most dominant products. Thus, the advantage of using furfural in the initial lignin solvent is because it regenerates itself from converting the hemicellulos into furfural during the fractionation processes. The advantage of butyl acetate is again solvent regeneration that takes place while making butyl acetate from butanol and acetic acid. Both furfural and butyl acetate are organic materials and separate easily from aqueous materials. So, by using butyl acetate in the first place, either alone or with less, fresh butanol each time the process is performed, about 50% more butyl acetate is recovered as a result. Since the market price of butanol and butyl acetate are almost the same, the process is cost efficient.

As explained above, in the presence of free butanol in the solution, one mole of acetic acid (60 g) plus one mole of butanol (74 g), produces one mole of butyl ester (116 g) for a net gain of 42 g (56.75% or about ~57% or generally about 60%) organic solvent (since butyl acetate is a lignin solvent too). Herein, organic solvent refers to the lignin dissolving chemical. So, while butyl acetate by itself is a good solvent for lignin, application of butanol along with butyl acetate can convert part of the hemicellulose to acetic acid, and convert the acetic acid and fresh butanol to butyl ester at about 56% to 57% gain by one form. This lowers the amount of fresh solvent needed and raises the production of organic solvent. In a similar parallel reaction, 1kg of biomass feedstock produces about 0.25 kg of furfural that is also a solvent for lignin, and therefore reduces the need for more fresh organic solvent.

Sample F—Furfural as Organic Solvent:

For sample F, the experiment was carried out at 178° C., 100 PSI Ar for 30 min., but was otherwise the same as that performed for Example 2 except with furfural as the lignin dissolving chemical in the initial lignin solvent. With furfural solvent, 13.23% lignin was extracted by this process, and 47.18% pulp yield was obtained. The detailed data is shown in Table 5 above.

The following observations are made:
1. Furfural can be used as a solvent for delignification of biomass.
2. Application of furfural as the solvent produces more 2-furancarboxaldehyde, 5-methyl than that produced by using butanol.
3. Application of furfural as the solvent produces more 2-furancarboxaldehyde, 5-(hydroxymethyl) than that produced by using butanol.
4. Application of furfural as the solvent extracts more lignin from biomass than that extracted by using butanol.
5. Since furfural is produced during the fractionation process, furfural is a self-sustaining solvent.

Since furfural is being generated as part of the fractionation process, using furfural as a solvent requires less fresh solvent to be used, and in fact will produce surplus solvent that can be reused for a new initial lignin solvent for a new biomass or may be extracted and sold.

As shown by Experiment 5 then, it will be appreciated that the lignin dissolving chemical in the initial lignin solvent may be an organic ester, and in one example butyl acetate, an organic furan such as furfural, or a mixture of both organic esters and organic furans, and in one example, a combination of both butyl acetate and furfural. As explained above, these lignin dissolving chemicals may or may not be combined with butanol.

Sample WB17

Distilled Bio Oil as Aqueous Solvent:

For sample WB17, the experiment was performed the same as that performed for Example 2 except with a solvent having 17 g distilled bio oil, 30 g furfural (liquid to solid by wt=5; water in biomass plus distilled bio oil:furfural=1:1 by wt), and 0.36 g sulfuric acid, and wood chips. The experiment was carried out at 178° C., 100 PSI Ar for 30 min and 535 rpm. With this bio-oil solvent, 10.85% lignin was extracted by this process, and 31.4% pulp yield was obtained. The details are provided on Table 4 above.

The following observations are made:
1. Bio-oil distillate used in this process as a solvent includes approximately 55% acetic acid, and the acetic acid reacted with butanol to produce butyl acetate.
2. Bio-oil distillate can be used a solvent to fractionate the biomass.

Thus, bio-oil also may be used alone, combined with butanol, or combined with any of the other compounds or chemicals described herein and used as the lignin dissolving chemical.

EXAMPLE 6

Use of Organic Acid (Acetic Acid)

For Example 6, instead of using a bio-oil to increase the amount of acetic acid in the system, the same process was performed as that of Example 2 (Sample WB1) except that here 18.6 g of acetic acid was used instead of sulfuric acid to mix with a butanol-based lignin solvent and wood chips. The experiment was carried out at 178° C., 100 PSI Ar, pH 1.12 and 413 rpm. Using Acetic Acid, 7.16% lignin was extracted by this process, and 56.871% pulp yield was obtained. The details of the chemicals produced are provided below on Table 6.

TABLE 6

Effects of using Acetic Acid

| Test Conditions, Test Number >>> | WB1 | WB9 | |
|---|---|---|---|
| Temperature | 178 | 178 | Constant |
| Time | 30 min | 30 min | Constant |
| Pressure (Pi) | 100 PSI | 100 PSI | Constant |
| Solvent butanol:water (1:1 by wt) | 1:1 | 1:1 | Constant |
| Acid | H2SO4 | acetic acid | Variable |
| Feedstock, woodchips | W | W | Constant |
| Gas/oxidants | Ar | Ar | Constant |
| Solvent to solid ratio | 5 | 5 | Constant |

| Data | g/L WB1 | g/L WB9 | |
|---|---|---|---|
| Acetic acid | 6.86 | 155.52 | ** |
| Butanol | 372.80 | 411.00 | Base |
| Formic acid, butyl ester | 0.00 | 370.98 | ** |
| Butyl acetate | 19.79 | 14.68 | * |
| Furfural | 21.77 | 0.00 | * |
| n-butyl ether | 1.08 | 0.00 | * |
| Propanoic acid, 1-methylpropyl ester | | | |
| Propanoic acid, butyl ester | | | |
| 2-furancarboxaldehyde, 5-methyl | 1.42 | 0.00 | * |
| Butanoic acid, butyl ester | | | |
| Propanoic acid, 2-hydroxy-, butyl ester | 1.42 | 0.00 | * |
| Oxirane, pentyl | | | |
| Morpholine | 1.21 | 0.86 | * |
| Butane, 1-(ethenyloxy) | | | |
| Phenol, 2-methoxy | 0.65 | 0.00 | * |
| 2-furancarboxaldehyde, 5-(hydroxymethyl) | 2.11 | 0.00 | * |
| Butane, 1,1-dibutoxy | 0.60 | 0.00 | * |
| Pentanoic acid, 4-oxo-, butyl ester (levulinic acid, butyl ester) | 0.00 | 0.00 | |
| 5-acetoxymethyl-2-furaldehyde | 0.00 | 0.00 | |
| Vanillin | 1.16 | 0.00 | * |
| Phenol, 2-methoxy-4-propyl (homovanillyl alcohol) | 0.00 | 0.00 | |

TABLE 6-continued

Effects of using Acetic Acid

| Test Conditions, Test Number >>> | WB1 | WB9 |
|---|---|---|
| 2-butenoic acid, hexyl ester | 0.00 | 0.00 |
| grams/liter (g/l) >>>>>> | 430.88 | 953.03 |
| Lignin as % of total liquor | 11.33% | 7.16% |
| Water 17.5% (close to theoretical value) | 17.50% | 17.50% |

The following observations are made:
1. Application of acetic acid produced more butyl ester than that produced by sulfuric acid (see ** on Table 6)
2. Acetic Acid does not produce Furfural. Using Ion Chromatography (IC), C5 sugar yield was the same for both acids. This indicates that C5 sugars produced in the IC are in the oligomeric form (in other words, IC cannot detect oligomers).
3. Application of Acetic Acid reduces or eliminates dip fragmentation, and as a result, fewer products and fewer amounts of products were formed when Acetic Acid used as an acid (see * on Table 6).
4. Acetic Acid can be used as a partial or whole substitute for Sulfuric Acid to promote Butyl Acetate production.

EXAMPLE 7

Experiments were performed to compare the effect of different raw materials. The same process as in Example 2 (sample WB1) was used here except that the raw material used for the biomass was grass (sample WB11), corn stover (sample WB12), bark (sample Bark), and bagasse (sample Bagasse). While the detailed data is provided below on Table 7 for all of these alternatives, a separate analysis was not provided for bagasse below.

Sample WB11: Use of Grass as Biomass

With grass forming the biomass (12 g of grass as the raw material which is the same mass of biomass as used for Example 2), the experiment was carried out at 178° C., 100 PSI Ar at pH 1.12 and 451 rpm. 4.66% lignin was extracted by this process, and 7.5725% (about 7.5%) pulp yield was obtained.

TABLE 7

Effects of Raw Materials

| Test Conditions, Test No.>> | WB1 | WB11 | WB12 | Bark | Bag. | |
|---|---|---|---|---|---|---|
| Temperature | 178 | 178 | 178 | 178 | 178 | Constant |
| Time (min) | 30 | 30 | 30 | 30 | 30 | Constant |
| Pressure (PSI) | 100 | 100 | 100 | 100 | 100 | Constant |
| Solvent butanol:water (1:1 by wt) | 1:1 | 1:1 | 1:1 | 1:1 | 1:1 | Constant |
| Acid | H2SO4 | H2SO4 | H2SO4 | H2SO4 | H2SO4 | Constant |
| Feedstock | Wood-chips | grass | corn stover | Bark | Bagasse | variable |
| Gas/oxidants | Ar | Ar | Ar | Ar | Ar | Constant |
| Solvent to solid ratio | 5 | 5 | 5 | 5 | 5 | Constant |
| Data | g/L | g/L | g/L | g/L | g/L | |
| Acetic acid | 6.86 | 1.29 | 2.07 | 7.11 | 0.91 | |
| Butanol | 372.80 | 326.00 | 375.60 | 355.00 | 353.80 | Base |
| Formic acid, butyl ester | 0.00 | 0.00 | 4.65 | 0.00 | 11.81 | |
| Butyl acetate | 19.79 | 1.42 | 13.06 | 8.15 | 18.62 | |
| Furfural | 21.77 | 2.31 | 18.68 | 21.85 | 20.61 | |
| n-butyl ether | 1.08 | 0.00 | 2.70 | 2.34 | 5.86 | |
| Propanoic acid, 1-methylpropyl ester | 0.00 | 0.00 | 0.00 | 0.00 | 0.00 | |
| Propanoic acid, butyl ester | 0.00 | 0.00 | 0.00 | 0.00 | 0.00 | |
| 2-furancarboxaldehyde, 5-methyl | 1.42 | 0.00 | 0.00 | 4.08 | 0.56 | |
| Butanoic acid, butyl ester | 0.00 | 0.00 | 0.00 | 0.00 | 0.00 | |
| Propanoic acid, 2-hydroxy-, butyl ester | 1.42 | 0.00 | 0.00 | 1.99 | 0.65 | |
| Oxirane, pentyl | 0.00 | 0.00 | 0.00 | 0.00 | 0.00 | |
| Morpholine | 1.21 | 0.00 | 0.00 | 1.00 | 0.00 | |
| Butane, 1-(ethenyloxy) | 0.00 | 0.00 | 0.00 | 0.00 | 0.00 | |
| Phenol, 2-methoxy | 0.65 | 0.00 | 0.00 | 0.00 | 0.00 | |
| 2-furancarboxaldehyde, 5-(hydroxymethyl) | 2.11 | 0.00 | 5.66 | 4.12 | 1.51 | |
| Butane, 1,1-dibutoxy | 0.60 | 0.00 | 1.61 | 3.77 | 0.95 | |
| Pentanoic acid, 4-oxo-, butyl ester (levulinic acid, butyl ester) | 0.00 | 0.00 | 0.00 | 0.00 | 6.90 | |
| 5-acetoxymethyl-2-furaldehyde | 0.00 | 0.00 | 0.00 | 0.00 | 0.00 | |
| Vanillin | 1.16 | 0.00 | 2.20 | 6.50 | 7.29 | |
| Phenol, 2-methoxy-4-propyl (homovanillyl alcohol) | 0.00 | 0.00 | 0.00 | 0.00 | 0.00 | |

TABLE 7-continued

| Effects of Raw Materials | | | | | |
|---|---|---|---|---|---|
| Test Conditions, Test No.>> | WB1 | WB11 | WB12 | Bark | Bag. |
| 2-butenoic acid, hexyl ester | 0.00 | 0.00 | 0.00 | 0.00 | 0.00 |
| g/l>>>>>> | 430.88 | 331.03 | 426.22 | 415.92 | 429.46 |
| Lignin as % of total liquor | 11.33% | 4.66% | 9.37% | 6.50% | 12.03% |
| Water 17.5% (close to theoretical value) | 17.50% | 17.50% | 17.50% | 17.50% | 17.50% |

The following observations are made:
1. Organosolv based delignification can produce chemicals from various biomass feed stocks such as wood, grass, corn stover, bark, and bagasse. This indicates many more raw materials may be used for delignification.
2. Maximum lignin was extracted from the woodchips and bagasse. This is due to relatively more lignin being present in the wood chips and leftover sugar cane stalk.
3. Bagasse produced the most vanillin.
4. Woodchips produced the most Butyl Acetate and Furfural.

Sample WB12:
Use of Corn Stover as Biomass
For this experiment, the reactor mixture included 12 g Oven Dry corn stover and solvent with 30 g water, 30 g butanol (liquid to solid by wt=5; water:butanol=1:1 by wt), 0.36 g sulfuric acid. Otherwise, the process was the same as that for Example 2 except that here, the experiment was carried out at 178° C., 100 PSI Ar, pH 1.12 and 451 rpm. With the corn stover as the biomass, 9.37% lignin was extracted in this process, and 21.056% pulp yield was obtained. The details are shown above on Table 6.

The following observations are made: corn stover produces more sugar in the aqueous layer than that produced by wood chips. This also produced more sugar from the pulp than that produced by wood chips. Corn has less lignin than wood.

Sample Bark:
Use of Bark as Biomass
For this experiment, the reactor mixture included 20 g oven dry bark, and a solvent with 50 g water, 50 g butanol (liquid to solid by wt=5; water:butanol=1:1 by wt), and 0.36 g sulfuric acid. Otherwise, the process was the same as that of Example 2 except that the experiment was carried out at 178° C., 100 PSI Ar, pH 1.12. With Bark as the biomass, 6.5% lignin was extracted by this process, and 52.6% pulp yield was obtained. The details of the parameters and the chemicals produced are shown above on Table 6. The resulting pulp fiber was subjected to enzymatic hydrolysis using CTec-2 which yielded 10 g/L sugar (16% solid to solid conversion).

The following observations are made:
1. Bark produced more furfural, propanoic acid derived chemicals, and 2-furancarboxaldehyde, 5-(hydroxymethyl) than wood chips.
2. Bark produced more vanillin than that produced by woodchips.

Sample Bagasse: Further analysis for Bagasse is not provided.

EXAMPLE 8

Effect of Atmosphere

The same parameters used for Example 2 (Sample WB1) were used here including the content of the biomass and Butanol-based lignin solvent. Except here, the autoclave was purged with Ar two times prior to being pressurized with varying gasses. To evaluate the effect of atmosphere on the lignin extraction process, three different experiments were carried out using Ar, O2 (Sample WB13), CO2 (Sample WB14), and H2 (Sample WB15). All the experiments were carried out at 178° C. for 100 PSI at the selected gas for 30 min and at pH 1.12. Table 8A shows the resulting lignin extraction and pulp yield. Table 8B provides the details of the parameters and the chemicals produced from the process.

TABLE 8A

| Effect of Atmosphere | | | |
|---|---|---|---|
| Samples | atmosphere | Lignin % | Pulp yield % |
| WB1 | Ar | 11.33 | 55.38 |
| WB13 | O2 | 12.42 | 38.24 |
| WB14 | CO2 | 15.6 | 37.9 |
| WB15 | H2 | 12.87 | 34.37 |

TABLE 8B

| Test Conditions, Test Number >>> | WB1 | WB13 | WB14 | WB15 | |
|---|---|---|---|---|---|
| Temperature | 178 | 178 | 178 | 178 | Constant |
| Time (min) | 30 | 30 | 30 | 30 | Constant |
| Pressure (PSI) | 100 | 100 | 100 | 100 | Constant |
| Solvent butanol:water (1:1 by wt) | 1:1 | 1:1 | 1:1 | 1:1 | Constant |
| Acid | H2SO4 | H2SO4 | H2SO4 | H2SO4 | Constant |
| Feedstock, woodchips | W | W | W | W | Constant |
| Gas/oxidants | Ar | O2 | CO2 | H2 | variable |
| Solvent to solid ratio | 5 | 5 | 5 | 5 | Constant |

TABLE 8B-continued

| Test Conditions, Test Number >>> | WB1 | WB13 | WB14 | WB15 | |
|---|---|---|---|---|---|
| Data | g/L | g/L | g/L | g/L | |
| Acetic acid | 6.86 | 5.36 | 1.40 | 1.24 | |
| Butanol | 372.80 | 367.80 | 76.57 | 78.97 | Base |
| Formic acid, butyl ester | 0.00 | 24.40 | 1.91 | 1.90 | |
| Butyl acetate | 19.79 | 37.80 | 7.72 | 7.19 | |
| Furfural | 21.77 | 32.35 | 7.28 | 6.25 | |
| n-butyl ether | 1.08 | 5.30 | 0.61 | 0.81 | |
| Propanoic acid, 1-methylpropyl ester | | 0.00 | 0.00 | 0.00 | |
| Propanoic acid, butyl ester | | 0.00 | 0.00 | 0.00 | |
| 2-furancarboxaldehyde, 5-methyl | 1.42 | 2.25 | 0.41 | 0.35 | |
| Butanoic acid, butyl ester | | 0.00 | 0.00 | 0.00 | |
| Propanoic acid, 2-hydroxy-, butyl ester | 1.42 | 0.00 | 0.31 | 0.25 | |
| Oxirane, pentyl | | 0.00 | 0.00 | 0.00 | |
| Morpholine | 1.21 | 2.85 | 0.14 | 0.15 | |
| Butane, 1-(ethenyloxy) | | 0.00 | 0.00 | 0.00 | |
| Phenol, 2-methoxy | 0.65 | 0.00 | 0.00 | 0.00 | |
| 2-furancarboxaldehyde, 5-(hydroxymethyl) | 2.11 | 4.10 | 1.11 | 0.93 | |
| Butane, 1,1-dibutoxy | 0.60 | 11.10 | 0.36 | 0.29 | |
| Pentanoic acid, 4-oxo-, butyl ester (levulinic acid, butyl ester) | 0.00 | 0.00 | 0.44 | 0.34 | |
| 5-acetoxymethyl-2-furaldehyde | 0.00 | 0.00 | 0.00 | 0.00 | |
| Vanillin | 1.16 | 5.85 | 1.41 | 1.20 | |
| Phenol, 2-methoxy-4-propyl (homovanillyl alcohol) | 0.00 | 0.00 | 0.11 | 0.09 | |
| 2-butenoic acid, hexyl ester | 0.00 | 0.00 | 0.11 | 0.03 | |
| grams/liter (g/l) >>>>>> | 430.88 | 499.16 | 99.89 | 99.99 | |
| Lignin as % of total liquor | 11.33% | 12.42% | 15.60% | 12.87% | |
| Water 17.5% (close to theoretical value) | 17.50% | 17.50% | 17.50% | 17.50% | |

The following observations are made:
1. Carbon dioxide is soluble in water and reversibly converts to $H_2CO_3$ (carbonic acid). Carbonic acid assists to increase lignin extraction, and as a result, the most lignin is extracted with an atmosphere of $CO_2$.
2. Even though CO2 atmosphere extracted the most lignin, the resultant pulp did not produce any more sugar than that produced by the other atmospheres.
3. A condensation reaction of butanol to produce butane, 1,1-dibutoxy is favored by the presence of O2.
4. Vanillin production is lessened in the presence of argon compared to the other atmospheres. Inert atmosphere (Ar) protects lignin from the oxidative cleavage to produce vanillin.
5. O2 atmosphere increases production of almost all of the produced chemicals such as formic acid, butyl acetate, furfural, and so forth shown above on Table 7B.

EXAMPLE 9

Effect of Amount of Solvent

The process is the same as that of Example 2 (WB1) except that here the butanol-based solvent is provided in different ratios relative to the biomass. To evaluate the effect of the amount of solvent, three different experiments were carried out using solid to liquid ratio of 1:5 (WB1 repeated from Example 2), 1:8 (WB7), and 1:12 (WB8). All the experiments were carried out at 178° C., 100 PSI Ar 30 min at pH 1.12. Table 9A shows the resulting amount of extracted lignin and the pulp yield for each ratio, and Table 9B shows the details of the parameters and chemicals produced from the process.

TABLE 9A

Effect of Solvent Amount

| Ratio | Lignin % | Pulp yield % |
|---|---|---|
| 1:5 | 11.33 | 55.38 |
| 1:8 | 7.76 | 37.39 |
| 1:12 | 4.9 | 38.8 |

TABLE 9B

Effect of Solvent Amount

| Test Conditions, Test Number >>> | WB1 | WB7 | WB8 | |
|---|---|---|---|---|
| Temperature | 178 | 178 | 178 | Constant |
| Time | 30 min | 30 min | 30 min | Constant |
| Pressure (Pi) | 100 PSI | 100 PSI | 100 PSI | Constant |
| Solvent butanol:water (1:1 by wt) | 1:1 | 1:1 | 1:1 | Constant |
| Acid | H2SO4 | H2SO4 | H2SO4 | Constant |
| Feedstock, woodchips | W | W | W | Constant |

TABLE 9B-continued

Effect of Solvent Amount

| Test Conditions, Test Number >>> | WB1 | WB7 | WB8 | |
|---|---|---|---|---|
| Gas/oxidants | Ar | Ar | Ar | Constant |
| Solvent to solid ratio | 5 | 8 | 12 | variable |
| Data | g/L WB1 | g/L WB7 | g/L WB8 | |
| Acetic acid | 6.86 | 6.46 | 5.02 | * |
| Butanol | 372.80 | 391.63 | 370.50 | Base |
| Formic acid, butyl ester | 0.00 | 0.00 | 0.00 | |
| Butyl acetate | 19.79 | 20.07 | 14.56 | * |
| Furfural | 21.77 | 21.34 | 16.40 | * |
| n-butyl ether | 1.08 | 2.41 | 2.64 | |
| Propanoic acid, 1-methylpropyl ester | | | | |
| Propanoic acid, butyl ester | | | | |
| 2-furancarboxaldehyde, 5-methyl | 1.42 | 1.27 | 0.54 | * |
| Butanoic acid, butyl ester | | | | |
| Propanoic acid, 2-hydroxy-, butyl ester | 1.42 | 1.18 | 0.67 | * |
| Oxirane, pentyl | | | | |
| Morpholine | 1.21 | 1.32 | 1.38 | |
| Butane, 1-(ethenyloxy) | | | | |
| Phenol, 2-methoxy | 0.65 | 0.00 | 0.00 | |
| 2-furancarboxaldehyde, 5-(hydroxymethyl) | 2.11 | 3.46 | 2.80 | |
| Butane, 1,1-dibutoxy | 0.60 | 1.05 | 1.42 | ** |
| Pentanoic acid, 4-oxo-, butyl ester (levulinic acid, butyl ester) | 0.00 | 0.73 | 0.00 | |
| 5-acetoxymethyl-2-furaldehyde | 0.00 | 0.00 | 0.00 | |
| Vanillin | 1.16 | 2.64 | 2.05 | ** |
| Phenol, 2-methoxy-4-propyl (homovanillyl alcohol) | 0.00 | 0.68 | 0.42 | |
| 2-butenoic acid, hexyl ester | 0.00 | 0.36 | 0.00 | |
| g/l>>>>>> | 430.88 | 454.61 | 418.40 | |
| Lignin as % of total liquor | 11.33% | 7.76% | 4.90% | |
| Water 17.5% (close to theoretical value) | 17.50% | 17.50% | 17.50% | |

The following observations are made:
1. Chemicals can be produced using a wide range of solid to solvent ratios.
2. More vanillin is produced when the extracted lignin is diluted to 1:8 and 1:12. Higher solvent ratios increase the lignin dispersement for oxidative degradation of lignin to vanillin (**).
3. Although lignin concentration (% of lignin in the total solvent versus merely the liquor) decreases with an increase in amount of solvent, the amount of lignin extracted remains relatively the same or similar. The concentration reduction is due to a dilution factor. Thus, the delignification process can be done using a wide range of solid to solvent ratios.
4. Even with a dilution factor of 1:8, higher concentrations of C5 sugars were produced than the 1:5 ratio, which indicates that more monomeric C5 sugars were formed when 1:8 solvent was used compared to that with the 1:5 solvent ratio.
5. The 1:5 ratio is found to be the most cost effective ratio for producing more self-sustaining solvent although producing less of some of the other resulting chemicals.

EXAMPLE 10

Solvent Gain Due to the Production of Chemicals

Experiments were performed to determine whether more solvent was produced than was used for the solvent in the first place.

(1) Lab Test:

Experiments were performed in a batch reactor (mechanically stirred-250 mL stainless steel autoclave) using 12 g oven dry wood chips. In this experiment, 48 g water; 48 g butanol (water:butanol=1:1 by wt), 0.36 g sulfuric acid and wood chips were added to the reactor. The autoclave was then purged two times with Ar prior to being pressurized with the required gas and heated to the required temperature for the delignification process. The autoclave temperature was measured by a type-K Omega thermocouple placed inside the reactor body. The experiments were carried out at 178° C., 100 PSI, Ar atmosphere, and for a fractionation and circulation time of 30 min, and at pH 1.12, until an initial lignin solvent was transformed into a circulation solvent.

Once the time period was complete, forced air and cold water were used to facilitate cooling. Once the reactor reached room temperature, the pulp and solvent were removed from the reactor and separated by gravity filtration. The pulp was squeezed by hand to yield additional solvent before it was subjected to water washing. The collected solvents were then allowed to settle down in a separating funnel to separate the aqueous and liquor fractions. One gram of liquor was then dried for an hour at about 100° C. to evaluate the amount of lignin extracted from the wood chips.

After the test, 72 g of liquor was obtained, which is 24 g higher (50% gain) than what was used (48 g butanol).

(2) Pilot Test:

Experiments were performed in a pilot continuous bed reactor. For these experiments, 40 kg wood chips at 50% solid content (20 Kg biomass and 20 Kg water content), 30 kg water, 50 Kg butanol (liquid to solid by wt=5; water:butanol=1:1 by wt), 0.346 kg sulfuric acid were added to the reactor. The reactor was pressurized with N2 100 PSI before the start of the experiment. The heating was done using a heating exchanger and the fluid was circulated using a pump. The experiment was carried out at 178° C., 100 PSI Ar, pH 1.12 and 30 min. At the completion of the experiment, the reactor was cooled down. Once the reactor reached room temperature, the pulp and solvent were removed from the reactor and separated by gravity filtration. The pulp was centrifuged to yield additional solvent before it was subjected to water washing. The collected solvents were then allowed to settle down in a separating funnel to separate the aqueous and liquor fractions. Ten grams of liquor was then dried for an hour at about 100° C. to evaluate the amount of lignin extracted from the wood chips.

A total 61 kg of liquor was collected. The total organic solvent gained was 11 kg, which is equivalent to 22% of the total organic solvent used, due to the formation of organic chemicals form the biomass components. For this experiment, 7.9% lignin was observed in the liquor, and 38.86% pulp yield was obtained with a Kappa number of 70.

EXAMPLE 11

Reusing the Liquor

The liquor (organic solvent) obtained from a typical fractionation example was vacuum distilled (50-80° C.) to separate the solvent (butanol and other chemicals formed during the fractionation process and all together are called organic solvent) and the solid lignin. Tests were carried out to evaluate whether the liquor and the aqueous layer water can be reused in an initial lignin solvent for fractionation of a new biomass in the reactor (or the next cycle).

(1) Lab Test:

Experiments were performed in a batch reactor (mechanically stirred-250 mL stainless steel autoclave) using 36.5 g wood chips (20 g oven dry). In this experiment, 33.5 g recycled aqueous layer water; 50 g distilled recycled liquor (recycled aqueous layer water:distilled recycled liquor=1:1 by wt), 0.36 g sulfuric acid and wood chips were added to the reactor. The autoclave was then purged two times with Ar prior to being pressurized with the required gas and heated to the required temperature for the delignification process. The autoclave temperature was measured by a type-K Omega thermocouple placed inside the reactor body. The experiments were carried out at 178° C., 100 PSI Ar 30 min at pH 1.16, and an initial lignin solvent was circulated over a biomass to form a circulation solvent.

At the completion of the time period for recycling the circulation solvent, forced air and cold water were used to facilitate cooling. Once the reactor reached room temperature, the pulp and solvent were removed from the reactor and separated by gravity filtration (separation tank). The pulp was squeezed by hand to yield additional solvent before it was subjected to water washing. The collected solvents were then allowed to settle down in a separating funnel to separate the aqueous and liquor fractions. One gram of liquor was then dried for an hour at about 100° C. to evaluate the amount of lignin extracted from the wood chips.

After the test, 58 g of liquor (9% lignin), 27.3 g aqueous layer, and 33.7 g pulp (8.589 g oven dry) was obtained. This example shows that the chemicals formed in this process can be collected in the liquor, and can be used as a lignin dissolving chemical in an initial lignin solvent for the next run over a new biomass. This process will make the fractionation process a self-sustaining recycling process.

(2) Pilot Test:

In another example, experiments were conducted to determine whether the formed chemicals, along with the recovered organic solvent (including produced lignin dissolving chemicals), can be reused as the initial lignin solvent for the next cycle for a new biomass while using a continuous bed reactor. The pilot test was carried out as follows.

Experiments were performed in a pilot continuous bed reactor. In this experiment, 37.09 kg wood chips at 54% solid content (20 Kg biomass and 17.1 Kg water content), 32.91 kg water, 50 Kg distilled liquor (liquid to solid by wt=5; water: organic solvents=1:1 by wt), 0.346 kg sulfuric acid and bark were added to the reactor. The reactor was pressurized with N2 100 PSI before the start of experiment. The heating was done using a heating exchanger and the fluid was circulated using a pump. The experiment was carried out at 178° C., 100 PSI Ar, pH 1.12 and 30 min. At the completion of the experiment, the reactor was cooled down. Once the reactor reached room temperature, the pulp and solvent were removed from the reactor and separated by gravity filtration. The pulp was centrifuged to yield additional solvent before it was subjected to water washing. The collected solvents were then allowed to settle down in a separating funnel (separation tank for example) to separate the aqueous and liquor fractions. Ten grams of liquor was then dried for an hour at about 100° C. to evaluate the amount of lignin extracted from the wood chips.

For this experiment, 7.47 wt % lignin was observed in the liquor, which is 3.18 kg (15.95 wt % from the total biomass). Also, 39% pulp yield was obtained, which is more than 90% theoretical production.

EXAMPLE 12

Experiments were performed to determine whether oxidants effect chemical production and should replace, or be added to, the Ar atmosphere.

TABLE 10

Effects of Oxidants (no oxidant, O2, and O2/H2O2)

| Test Conditions, Test Number >>> | WB1 | WB13 | WB16 | |
|---|---|---|---|---|
| Temperature | 178 | 178 | 178 | Constant |
| Time (min) | 30 min | 30 min | 30 min | Constant |
| Pressure (PSI) | 100 PSI | 100 PSI | 100 PSI | Constant |
| Solvent butanol:water (1:1 by wt) | 1:1 | 1:1 | 1:1 | Constant |
| Acid | H2SO4 | H2SO4 | H2SO4 | Constant |
| Feedstock, woodchips | W | W | W | Constant |
| Gas/oxidants | Ar | O2 | O2/H2O2/ hydrite | variable |
| Solvent to solid ratio | 5 | 5 | 5 | Constant |
| Data | g/L | g/L | g/L | |
| Acetic acid | 6.86 | 5.36 | 0.00 | |
| Butanol | 372.80 | 367.80 | 76.75 | Base |
| Formic acid, butyl ester | 0.00 | 24.40 | 7.20 | |
| Butyl acetate | 19.79 | 37.80 | 3.57 | |
| Furfural | 21.77 | 32.35 | 2.08 | |
| n-butyl ether | 1.08 | 5.30 | 0.00 | |
| Propanoic acid, 1-methylpropyl ester | | 0.00 | 0.38 | |
| Propanoic acid, butyl ester | | 0.00 | 0.00 | |
| 2-furancarboxaldehyde, 5-methyl | 1.42 | 2.25 | 0.53 | |
| Butanoic acid, butyl ester | | 0.00 | 0.37 | |
| Propanoic acid, 2-hydroxy-, butyl ester | 1.42 | 0.00 | 0.00 | |
| Oxirane, pentyl | | 0.00 | 0.95 | |
| Morpholine | 1.21 | 2.85 | 0.00 | |
| Butane, 1-(ethenyloxy) | | 0.00 | 1.85 | |
| Phenol, 2-methoxy | 0.65 | 0.00 | 0.00 | |
| 2-furancarboxaldehyde, 5-(hydroxymethyl) | 2.11 | 4.10 | 0.13 | |
| butane, 1,1-dibutoxy | 0.60 | 11.10 | 4.05 | |
| pentanoic acid, 4-oxo-, butyl ester (levulinic acid, butyl ester) | 0.00 | 0.00 | 0.00 | |
| 5-acetoxymethyl-2-furaldehyde | 0.00 | 0.00 | 0.00 | |
| Vanillin | 1.16 | 5.85 | 0.22 | |
| phenol, 2-methoxy-4-propyl (homovanillyl alcohol) | 0.00 | 0.00 | 0.00 | |
| 2-butenoic acid, hexyl ester | 0.00 | 0.00 | 0.00 | |
| g/l>>>>>> | 430.88 | 499.16 | 98.08 | |
| Lignin as % of total liquor | 11.33% | 12.42% | 10.41% | |
| water 17.5% (close to theoretical value) | 17.50% | 17.50% | 17.50% | |

The following observations are made:
1. The presence of H2O2 and hydrate converts the acetic to formic, and subsequently the formic acid is converted to formic acid butyl acetate. Thus, H2O2 produced more formic acid butyl acetate than the other gases that do not use co-oxidants.
2. Application of co-oxidants such as H2O2 also promotes production of butyl ester, Oxirane-pentyl, butane-1-(ethenyloxy), butane-1-1-dibutoxy, and so forth as shown on Table 9 above.
3. Application of a co-oxidant such as H2O2 as an additive does not perform well compared to the other types of oxidants.

4. Adding oxidants in the form of O2 promotes overall production of chemicals.
5. Butanol condensation to butane, 1,1-dibutoxy is favored in the presence of oxidants.
6. Application of oxidants also increases production of formic acid, butyl acetate, furfural, 2-furancarboxaldehyde, 5-(hydroxymethyl), vanillin, and so forth, as shown on Table 10 above.

Thus, in one form, it is contemplated to combine an O2 atmosphere to the Ar atmosphere when desired.

While the foregoing written description of the invention enables one of ordinary skill to make and use what is considered presently to be the best mode thereof, those of ordinary skill will understand and appreciate the existence of variations, combinations, and equivalents of the specific exemplary embodiments and methods herein. The invention should therefore not be limited by the above described embodiments and methods, but by all embodiments and methods within the scope and spirit of the invention as claimed.

What is claimed is:

1. An organosolv process for producing bio-products by decomposing lignocellulosic materials comprising:
   providing an initial lignin solvent comprising:
      water,
      an acid, and
      a lignin dissolving chemical comprising butanol;
   placing the intial lignin solvent in contact with a biomass to form a circulation solvent comprising butanol, butyl acetate, and furfural; and
   recycling at least a portion of the circulation solvent by circulating the circulation solvent back into contact with the biomass for a period of time; and
   after the period of time, separating material from the circulation solvent.

2. The process of claim 1 wherein separating material comprises dividing an organic material portion, water insoluble lignin, and an aqueous solution portion from the circulation solvent.

3. The process of claim 2 comprising reusing at least a part of the organic material portion in an initial lignin solvent for a new biomass.

4. The process of claim 2 comprising reusing at least a part of the aqueous solution portion in an initial lignin solvent for a new biomass.

5. The process of claim 2 comprising mixing the lignin with one or more polymers to produce a polymeric object.

6. The process of claim 2 comprising mixing the lignin with one or more polymers as a colorant for a polymeric object.

7. The process of claim 1 comprising reusing at least part of the separated material in an initial lignin solvent for a new biomass without fermenting the part.

8. The process of claim 1 wherein the lignin dissolving chemical in the initial lignin solvent also comprises an organic ester.

9. The process of claim 1 wherein the lignin dissolving chemical in the initial lignin solvent also comprises butyl acetate.

10. The process of claim 1 wherein the lignin dissolving chemical in the initial lignin solvent also comprises an organic furan.

11. The process of claim 1 wherein the lignin dissolving chemical in the initial lignin solvent also comprises furfural.

12. The process of claim 1 wherein the lignin dissolving chemical in the initial lignin solvent also comprises butyl acetate and furfural.

13. The process of claim 1 comprising reusing at least butyl acetate and furfural in an organic material portion separated from a previously used circulation solvent.

14. The process of claim 1 comprising forming a pulp having fibers comprising cellulose.

15. The process of claim 1 wherein the acid in the initial lignin solvent comprises sulfuric acid.

16. The process of claim 1 wherein the acid in the initial lignin solvent comprises acetic acid.

17. The process of claim 1 wherein the time period is at least approximately 30minutes.

18. The process of claim 1 comprising contacting the solvent with the biomass in an atmosphere at an initial pressure above atmospheric pressure.

19. The process of claim 1 wherein the biomass comprises dry lignocellulosic material provided at a 1:5 ratio or higher with the solvent.

20. The process of claim 1 comprising heating the solvent in contact with the biomass in a reactor to a reactor cooking temperature of at least approximately 178° C.

21. The process of claim 1 comprising heating the solvent in contact with the biomass in a reactor to a high reactor cooking temperature approximately 225° C. to simultaneously fractionate the biomass and hydrolyze the fiber into sugar.

22. The process of claim 1 comprising adding $H_2O_2$ to the initial lignin solvent to produce butyltoxy materials.

23. The process of claim 1 comprising maintaining the contact between the initial lignin solvent and the biomass at a cooking pressure of about 100 psi and above.

24. The process of claim 1 comprising maintaining the contact between the initial lignin solvent and the biomass at a cooking temperature of about 178 degrees Celsius and above and forming a pulp with fibers from the biomass, and at least partially hydrolyzing the fibers.

25. The process of claim 1 comprising a solvent-to-dry biomass ratio of about 8:1 and above.

26. The process of claim 1 wherein the acid comprises acetic acid.

27. The process of claim 1 comprising placing the lignin solvent in contact with the biomass within an atmosphere comprising oxygen.

28. The process of claim 1 comprising forming carbonic acid by placing the solvent in contact with the biomass within a carbon dioxide atmosphere.

29. The process of claim 1 wherein the biomass comprises at least one of:
   grass,
   corn stover,
   bark, and
   bagasse.

30. An organosolv process for producing bio-products by decomposing lignocellulosic materials comprising:
   providing an initial lignin solvent comprising:
      water,
      an acid, and
      a lignin dissolving chemical comprising butanol, butyl ester, and furan;
   placing the initial lignin solvent in contact with a biomass to form a circulation solvent comprising butanol, butyl acetate, and furfural; and
   recycling at least a portion of the circulation solvent by circulating the circulation solvent back into contact with the biomass for a period of time; and
   after the period of time, separating material from the circulation solvent.

31. The process of claim 30 wherein the lignin dissolving chemical in the initial lignin solvent comprises approximately ⅓ each of butanol, a butyl ester, and an organic furan by weight.

32. An organosolv process for producing bio-products by decomposing lignocellulosic materials comprising:
- providing a first initial lignin solvent comprising:
  - water,
  - an acid comprising acetic acid, sulfuric acid, or both, and
  - a lignin dissolving chemical comprising butanol;
- placing the first initial lignin solvent in contact with a first biomass to form a circulation solvent comprising butanol, butyl ester, and furfural; and
- recycling at least a portion of the circulation solvent by circulating the circulation solvent back into contact with the biomass for a period of time;
- after the period of time, dividing the circulation solvent into an aqueous portion, an organic material portion, and lignin; and
- reusing at least a portion of the aqueous portion, the organic material portion, or both in an initial lignin solvent to be placed in contact with a new biomass.

33. The process of claim 32 wherein the circulation solvent is approximately ⅓ butanol, ⅓ butyl ester, and ⅓ furfural by weight.

34. The process of claim 32 the butyl ester or furfural or both are derived from the organic material portion, and the butanol is added from a separate source.

35. The process of claim 32 wherein the first initial lignin solvent also comprises butyl ester.

36. The process of claim 32 where in the first initial lignin solvent also comprises furfural.

37. The process of claim 32 wherein the first initial lignin solvent also comprises butyl ester and furfural.

* * * * *